(12) United States Patent
Blair et al.

(10) Patent No.: US 11,060,060 B2
(45) Date of Patent: Jul. 13, 2021

(54) METHOD OF MAKING TRABECULAR BONE

(71) Applicants: University of Pittsburgh—Of the Commonwealth System of Higher Education, Pittsburgh, PA (US); The United States Government as represented by the Department of Veterans Affairs, Washington, DC (US); University of Chicago, Chicago, IL (US); Washington University in St. Louis, St. Louis, MO (US)

(72) Inventors: Harry Colbert Blair, Pittsburgh, PA (US); Quitterie Larrouture, Pittsburgh, PA (US); Irina L. Tourkova, Pittsburgh, PA (US); Deborah J. Nelson, Riverside, IL (US); Paul Schlesinger, University City, MO (US)

(73) Assignees: University of Pittsburgh—Of the Commonwealth System of Higher Education, Pittsburgh, PA (US); The United States Government as represented by the Department of Veterans Affairs, Washington, DC (US); University of Chicago, Chicago, IL (US); Washington University, St. Louis, MO (US)

( * ) Notice: Subject to any disclaimer, the term of this patent is extended or adjusted under 35 U.S.C. 154(b) by 363 days.

(21) Appl. No.: 15/760,452

(22) PCT Filed: Sep. 16, 2016

(86) PCT No.: PCT/US2016/052277
§ 371 (c)(1),
(2) Date: Mar. 15, 2018

(87) PCT Pub. No.: WO2017/049178
PCT Pub. Date: Mar. 23, 2017

(65) Prior Publication Data
US 2018/0258399 A1 Sep. 13, 2018

Related U.S. Application Data

(60) Provisional application No. 62/219,480, filed on Sep. 16, 2015.

(51) Int. Cl.
*C12N 5/00* (2006.01)
*C12N 5/02* (2006.01)
*C12N 5/077* (2010.01)
*A01K 67/027* (2006.01)
*C12N 15/113* (2010.01)

(52) U.S. Cl.
CPC ........ *C12N 5/0654* (2013.01); *A01K 67/0276* (2013.01); *C12N 15/1138* (2013.01); *A01K 2217/058* (2013.01); *A01K 2217/075* (2013.01); *C12N 2310/14* (2013.01); *C12N 2310/531* (2013.01); *C12N 2501/999* (2013.01); *C12N 2506/1346* (2013.01); *C12N 2510/00* (2013.01); *C12N 2517/00* (2013.01); *C12N 2517/02* (2013.01)

(58) Field of Classification Search
CPC .......................... C12N 5/0654; A01K 67/0276
See application file for complete search history.

(56) References Cited

U.S. PATENT DOCUMENTS

2002/0065325 A1  5/2002  Lamb et al.
2004/0265837 A1  12/2004  Jentsch

OTHER PUBLICATIONS

Du (Feb. 2015, Int J Clin Exp Pathol, 8:1622-16330).*
Cuddapah (2010, Journal of Biological Chemistry, 285:11188-11196).*
Arpornmaeklong et al., "Phenotypic Characterization, Osteoblastic Differentiation, and Bone Regeneration Capacity of Human Embryonic Stem Cell-Derived Mesenchymal Stem Cells", Stem Cells and Development, 2009, pp. 955-968, vol. 18(7).
Blair et al., Calcium and bone disease, Biofactors, 2011, pp. 159-167, vol. 37(3).
Blair et al., "Calcium Signalling and Calcium Transport in Bone Disease", Subcell Biochem., 2007, pp. 539-562, vol. 45.
Blair et al., "Osteoclastic Bone Resorption by a Polarized Vacuolar Proton Pump", Science, 1989, pp. 855-857, vol. 245(4920).
Blair et al., "Passive chloride permeability charge coupled to H+-ATPase of avian osteoclast ruffled membrane", The American Physiological Society, 1991, pp. C1315-C1324.
Claud et al., "Platelet-activating factor-induced chloride channel activation is associated with intracellular acidosis and apoptosis of intestinal epithelial cells", Am J Physiol Gastrointest Liver Physiol, 2008, pp. G1191-G1200, vol. 294.
Dickerson et al., "Altered GABAergic function accompanies hippocampal degeneration in mice lacking ClC-3 voltage-gated chloride channels", Brain Research, 2002, pp. 227-250, vol. 958.
Geraerts et al., "Upscaling of lentiviral vector production by tangential flow filtration", The Journal of Gene Medicine, 2005, pp. 1299-1310, vol. 7.
Guzman et al., "ClC-3 Is an Intracellular Chloride/Proton Exchanger with Large Voltage-Dependent Nonlinear Capacitance", ACS Chem. Neurosci., 2013, pp. 994-1003, vol. 4.
Jakob et al., "Perspective on the Evolution of Cell-Based Bone Tissue Engineering Strategies", Eur Surg Res., 2012, pp. 1-7, vol. 49.
Kornak et al. "Loss of the ClC-7 Chloride Channel Leads to Osteopetrosis in Mice and Man", Cell, 2001, pp. 205-215, vol. 104.
Larrouture et al., "Chloride-hydrogen antiporters ClC-3 and ClC-5 drive osteoblast mineralization and regulate fine-structure bone patterning in vitro", Physiological Reports, 2015, pp. 1-13, vol. 3(11).

(Continued)

*Primary Examiner* — Valarie E Bertoglio
(74) *Attorney, Agent, or Firm* — The WebbLaw Firm

(57) ABSTRACT

Provided herein are methods of producing trabecular bone material, such as trabecular bone or trabecular bone matrix and cells useful in preparing the trabecular bone material.

8 Claims, 9 Drawing Sheets

Specification includes a Sequence Listing.

(56) References Cited

OTHER PUBLICATIONS

Liu et al., "High Capacity NA+/H+ Exchange Activity in Mineralizing Osteoblasts", Journal of Cellular Physiology, 2011, pp. 1702-1712, vol. 226.

Liu et al., Na+/H+ Exchanger Regulatory Factor 1 (NHERF1) Directly Regulates Osteogenesis, The Journal of Biological Chemistry, 2012, pp. 43312-43321, vol. 287:52.

Magnusson et al., "Isoforms of Bone Alkaline Phosphatase: Characterization and Origin in Human Trabecular and Cortical Bone", Journal of Bone and Mineral Research, 1999, pp. 1926-1933, vol. 14(11).

Newman et al., "The Chemical Dynamics of Bone Mineral", The University of Chicago Press, 1958, pp. 473-474.

Palagano et al., "Buried in the Middle but Guilty: Intronic Mutations in the TCIRG1 Gene Cause Human Autosomal Recessive Osteopetrosis", Journal of Bone and Mineral Research, 2015, pp. 1814-1821, vol. 30(10).

Picollo et al., "Chloride/proton antiporter activity of mammalian CLC proteins ClC-4 and ClC-5", Nature, 2005, pp. 420-423, vol. 436.

Ravi et al., "Epidermal Growth Factor Activates the Rho GTPase-activating Protein (GAP) Deleted in Liver Cancer 1 via Focal Adhesion Kinase and Protein Phosphatase 2A", The Journal of Biological Chemistry, 2015, pp. 4149-4162, vol. 290(7).

Robinson et al., "Gene disruption of the calcium channel Orai1 results in inhibition of osteoclast and osteoblast differentiation and impairs skeletal development", Laboratory Investigation, 2012, pp. 1071-1083, vol. 92.

Robinson et al., "Estrogen inhibits RANKL-stimulated osteoclastic differentiation of human monocytes through estrogen and RANKL-regulated interaction of estrogen receptor-alpha with BCAR1 and Traf6", Experimental Cell Research, 2009, pp. 1287-1301, vol. 315.

Robinson et al., "FSH-receptor isoforms and FSH-dependent gene transcription in human monocytes and osteoclasts", Biochemical and Biophysical Research Communications, 2010, pp. 12-17, vol. 394.

Scheel et al., "Voltage-dependent electrogenic chloride/proton exchange by endosomal CLC proteins", Nature, 2005, pp. 424-427, vol. 436.

Schlesinger et al., "Osteoclastic acid transport: mechanism and implications for physiological and pharmacological regulation", Mineral and Electrolyte Metabolism, 1994, pp. 31-39, vol. 20.

Sena-Esteves et al., "Optimized large-scale production of high titer lentivirus vector pseudotypes", Journal of Virological Methods, 2004, pp. 131-139, vol. 122.

Shimada et al., "Expression and canalicular localization of two isoforms of the ClC-3 chloride channel from rat hepatocytes", Am J Physiol Gastrointest Liver Physiol, 2000, pp. G268-G276, vol. 279.

Silva et al., "The ClC-5 Knockout Mouse Model of Dent's Disease Has Renal Hypercalciuria and Increased Bone Turnover", Journal of Bone and Mineral Research, 2003, pp. 615-623, vol. 18(4).

Sobacchi et al., "Osteopetrosis: genetics, treatment and new insights into osteoclast function", Nat. Rev. Endocrinol., 2013, pp. 522-536, vol. 9.

Teti et al., "Cytoplasmic pH Regulation and Chloride/Bicarbonate Exchange in Avian Osteoclasts", J. Clin. Invest., 1989, pp. 227-233, vol. 83.

Wang et al., "Chloride Channel ClC-3 Promotion of Osteogenic Differentiation Through Runx2", Journal of Cellular Biochemistry, 2010, pp. 49-58, vol. 111.

Wang et al., "ClC-3 chloride channel functions as a mechanically sensitive channel in osteoblasts", Biochem. Cell Biol., 2015, pp. 558-565, vol. 93.

Wang et al., "NHERF1 Regulation of PTH-dependent Bimodal Pi Transport in Osteoblasts", Bone, 2013, pp. 268-277, vol. 52(1).

Wang et al., "Osteogenic role of endosomal chloride channels in MC3T3-E1 cells", Mol Cell Biochem, 2010, pp. 191-199, vol. 342.

Wein et al., "Lentivirus Delivery of shRNA Constructs into Osteoblasts", Methods in Molecular Biology, pp. 149-155, vol. 455.

GenBank: AF029347.1, Mus musculus chloride channel protein 3 (CLCN3) mRNA, complete cds, Jan. 7, 1998.

HGNC: 2021, HGNC Database, HUGO Gene Nomenclature Committee (HGNC), European Molecular Biology Laboratory, European Bioinformatics Institute (EMBL-EBI), Wellcome Genome Campus, Hinxton, Cambridge CB10 1SD, United Kingdom www.genenames.org.

Gene ID: 1182, "CLCN3 chloride voltage-gated channel 3 [*Homo sapiens* (human*)*", Gene, NCBI, Feb. 3, 2019, pp. 1-11.

Ensembl: ENSG00000109572, Daniel R. Zerbino, et al. Ensembl 2018.

Online Mendelian Inheritance in Man, OMIM®. Johns Hopkins University, Baltimore, MD. MIM No. 600580: Oct. 24, 2002.

UniProtKB—P51790 (CLCN3_HUMAN), Jan. 16, 2019, pp. 1-15.

NCBI Reference Sequence: NM_001243372.1, "*Homo sapiens* chloride voltage-gated channel 3 (CLCN3), transcript variant a, mRNA", Nucleotide, Feb. 23, 2019, pp. 1-6.

NCBI Reference Sequence: NP_001230301.1, H(+)/Cl(−) exchange transporter 3 isoform a [*Homo sapiens*], Protein, Nov. 4, 2018, pp. 1-3.

Gene ID: 12725, Clcn3 chloride channel, voltage-sensitive 3 [ *Mus musculus* (house mouse) ], Gene, Jan. 31, 2019, pp. 1-11.

NCBI Reference Sequence: NM_007711.3, "Mus musculus chloride channel, voltage-sensitive 3 (Clcn3), transcript variant a, mRNA", Nucleotide, Sep. 23, 2018, pp. 1-5.

NCBI Reference Sequence: NP_031737.1, "H(+)/Cl(−) exchange transporter 3 isoform a [Mus musculus]", Protein, Sep. 23, 2018, pp. 1-3.

\* cited by examiner

```
   1 atggagtctg agcagctgtt ccatagaggc tactatagaa acagctacaa cagcataacc
  61 agcgcgagta gcgatgagga gctcctagat ggagcaggtg ccattatgga ctttcagact
 121 tctgaagatg acaatttgtt agacggggac acagcagctg gaactcatta tacaatgaca
 181 aatggaggca gcattaatag ctctacacac ttgctggatc ttttagatga gcctatccca
 241 ggtgtcggta cctacgatga tttccatact attgactggg tgcgagagaa gtgtaaggac
 301 agagaaggc acagacggat caacagtaaa aaaaaagaat cagcatggga aatgacaaaa
 361 agtctgtatg acgcctggtc aggatggctt gtcgttacac tgacgggact ggcatcaggg
 421 gcactagctg gattgataga cattgctgct gactggatga ctgacctgaa ggagggcatc
 481 tgcctcagtg cattgtggta caaccatgaa cagtgttgtt ggggctctaa tgagacaacg
 541 tttgaagaga gggataaatg tccacagtgg aaaacatggg cagagttaat cattggccaa
 601 gcagagggcc ctggatctta tcatgaac tacatcatgt atatcttttg ggctttgagt
 661 tttgcctttc ttgcagtttc tttggtgaaa gtatttgctc catatgcctg tggctctgga
 721 attccagaga ttaaaactat tttgagtgga tttatcatca gaggatactt gggaaaatgg
 781 actttaatga ttaaaactat cacgttagtg ctggctgtgg catcaggttt gagtttagga
 841 aaagaaggtc ccctggtaca tgttgcctgc tgctgtggaa atatcttttc ctacctcttt
 901 ccaaagtata gcaccaatga agctaaaaag agggaggtgc tgtcagccgc ctcagctgct
 961 gggggtttctg tggcttttgg tgcaccgatc ggaggagttc tttttagctt ggaggaggtt
1021 agctattatt ttcctctcaa aactttatgg agatcatttt ttgctgctttt ggtggcagca
1081 tttgttttga gatccatcaa tccatttggt aacagccgtc tggtcctctt ttatgtggag
1141 tatcatacac catggtacct ttttgaactg tttcctttta ttctcctagg ggtatttgga
1201 gggctttggg gagcttttttt tattagggca aatattgcct ggtgtcgtcg acgcaagtcc
1261 accaaatttg gaaagtatcc tgttctcgaa gtcattattg ttgcagccat tactgctgtg
1321 atagccttcc ccaacccata cacaaggctc aacaccagtg aactgattaa agagctgttt
1381 acagattgtg ggccgttgga atcctcctct ctctgtgact acagaaatga catgaatgcc
1441 agtaaaattg tgacgatat cctgaccgt ccagcaggcg ttggagtata ttcagctatc
1501 tggcagttgt gcctagcgct catatttaaa ataataatga cagtattcac ttttggtatc
1561 aaggtcccgt caggcttgtt tatccccagc atggccattg gagccattgc agggagaatt
1621 gtggggatcg ctgtggagca gcttgcctac tatcaccacg actggtttat cttcaaggag
1681 tggtgtgagg tggggctga ctgcatcact cccgggctgt atgccatggt tggggctgct
1741 gcgtgcttag gtggtgtgac aagaatgact gtgtctctgg tggttattgt ttttgaactt
1801 actggaggct ggaatatat tgttcctctt atggctgcag taatgaccag taaatgggtt
1861 ggtgatgcct tggtaggga aggtatttat gaagcacaca tccgactaaa tgggtaccct
1921 ttcttggatg caaaagaaga attcactcat acaaccctgg ctgctgatgt tatgagacct
1981 cgaagaagtg accctccctt agctgttttg acacaggaca atatgacagt agatgacata
2041 gaaaacatga ttaatgaaac cagctataat ggctttcctg ttataatgtc aaaagaatct
2101 cagagattag tgggatttgc cctcagaaga gacctgacta ttgcaataga aagtgccaga
2161 aaaaaacaag aagggattgt tggcagttct cgggtgtgtt ttgcacagca tactccatct
2221 cttccagcag aaagtccacg gccattaaaa ctgagaagca tccttgacat gagccctttt
2281 acagtgacag accacacccc aatggagatt gtggtagaca tctttcgaaa gcttggtctg
2341 aggcagtgcc ttgtaactca caacggacgc ctccttggca ttataacaaa aaaagatatc
2401 ctccgtcata tggcccagac ggcaaaccaa gacccgctt caataatgtt caactga
```

Fig. 1

| Gene | GenBank | Forward | Reverse | bp |
|---|---|---|---|---|
| Actin | NM_007393 | 5'GATATCGCTGCGCTGGTCGTC (SEQ ID NO: 3) | 5'ACGGCAGCTCATTGTAGAAGGTGTG (SEQ ID NO: 4) | 275 |
| Alp | NM_007431 | 5'ATCGGAACAACCTGACTGACCCTT (SEQ ID NO: 5) | 5'ACCCTCATGATGTCCGTGGTCAAT (SEQ ID NO: 6) | 131 |
| Clcn3 | AF029347 | 5'CCAAGACCCCGCTTCAATAA (SEQ ID NO: 7) | 5'CGAGTCCCGCAGATTAAAGA (SEQ ID NO: 8) | 122 |
| Clcn5 | NM_016691 | 5'GAGGAGCCAATCCCTGGTGTA (SEQ ID NO: 9) | 5'TTGGTAATCTCTCGGTGCCTA (SEQ ID NO: 10) | 101 |
| Col1 | NM_007742 | 5'TTCTCCTGGCAAAGACGGACTCAA (SEQ ID NO: 11) | 5'AGGAAGCTGAAGTCATAACCGCCA (SEQ ID NO: 12) | 159 |
| Ocn | NM_007541 | 5'ACCATCTTTCTGCTCACTCTGCTG (SEQ ID NO: 13) | 5'TATTGCCCTCCTGCTTGGACATGA (SEQ ID NO: 14) | 117 |
| Runx2 | NM_001145920 | 5'-ATGATGACACTGCCACCTCTGAC (SEQ ID NO: 15) | 5'ACTGCCTGGGGGTCTGAAAAAGG (SEQ ID NO: 16) | 105 |

Fig. 2

METHOD OF MAKING TRABECULAR BONE

CROSS REFERENCE TO RELATED APPLICATIONS

This application is the United States national phase pf International Application No. PCT/US2016/052277 filed Sep. 16, 2016, and claims the benefit of U.S. Provisional Patent Application No. 62/219,480, filed Sep. 16, 2015, the disclosures of which are hereby incorporated in their entirety by reference.

STATEMENT REGARDING FEDERAL FUNDING

This invention was made with government support under grant Nos. AR065407 and AR055208, awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 1801424_ST25.txt. The size of the text file is 6,932 bytes, and the text file was created on Feb. 8, 2018.

Provided herein is a method of making trabecular bone.

Hypotheses describing the etiology of idiopathic osteoporosis include a smattering of incomplete tubular acidosis and calcium wasting hypotheses, but in most cases have no rationale for the finding of osteoporosis. There is a clear problem with osteoporosis not fitting known categories of matrix defects. This likely reflects the existence of many mineral transport defects that, if not lethal, have mild or moderate phenotypes. Since humans are long-lived, defects accumulate with time to produce skeletal fragility, and cases may have multi-factorial causes.

In an attempt to "close the loop" regarding one major incomplete system, acid elimination to drive mineralization to completion, Blair et al. (2011, Calcium and bone disease. *Biofactors* 37: 159-167) produced conclusive data that without CLC-3 and CLC-5, osteoblasts cannot mineralize in vitro. It is likely that for further in vivo studies, cell specific knockouts may be required; mutations of Clcn5 cause Dent's disease (Silva et al., 2003, The ClC-5 knockout mouse model of Dent's disease has renal hypercalciuria and increased bone turnover. *J Bone Miner Res* 18: 615-623) and constitutive CLC-3/CLC-5 double knockout animals are likely to be lethal.

Precedents in bone include that CLC-7 mediates exchange of extracellular $H^+$ for $Cl^-$ and is required for normal osteoclast function. In addition, in a singular study, Wang et al. (2010, Osteogenic role of endosomal chloride channels in MC3T3-E1 cells. *Mol Cell Biochem* 342: 191-199), CLCs 3, 4, and 5 were hypothesized to drive osteoblast differentiation. Each CLC, when over-expressed in MC3T3-E1 osteoblast-like cells, localized to peripheral membranes and was associated with increased mineralization, in the mineralization pattern seen in normal wild-type cells. Further, the same group recently showed that over-expressing CLC-3 in MC3T3-E1 rendered cells susceptible to mechanical force-induced up-regulation of bone markers (Wang et al. 2015, Chloride Channel Function as a Mechanical Sensitive Channel in Osteoblast. *Biochem Cell Biol* 2015 13 Jul. 10.1139/bcb-2015-0018 [e-published before print]).

Much further work is required fully to characterize outward proton transport with bone mineral formation. The $H^+$ gradient during mineral transport is minor, but "uphill"; bone matrix is maintained at about pH 7.6-7.8. The extracellular chloride concentration is unknown, and precipitation of mineral may leave a hypotonic solution, requiring aquaporins or another water transport mechanism. Further, a cation is required to drive $Cl^-/H^+$ exchange, since it is electrogenic. Potassium conductance is the likely candidate; a specific channel is not known, and there are many candidates. Additionally, chloride balance of the osteoblasts would be jeopardized by massive Cl/H exchange; a compensatory mechanism must exist, possibly a KCl symport. Proton balance is not a problem; transit of acid from the osteoblast is the function of NHE Na/H exchangers at the basolateral membranes of osteoblasts. In human mineralizing osteoblast cRNA screens high expression of both aquaporin and KCl symport transcripts are shown, but those will require specific study to validate the hypothesis that they fulfill support roles during bone synthesis in the isolated extracellular matrix compartment. There are many other specializations of osteoblasts, including high levels of expression of glutathione peroxidases and superoxide dismutases, which may be required to counteract free radical production during synthesis of bone matrix.

A lack of complete understanding of the mechanism of osteoporosis, and of bone formation in general, has resulted in a lack of suitable methods of preparing bone tissue, particularly trabecular bone tissue as a treatment for osteoporosis, traumatic injury to the bones or other defects or conditions that require a useful trabecular structure. A generation of attempts to make bone with suitable characteristics for surgical implants has fallen short. Despite numerous types of bioreactors containing many different types of supporting matrix or scaffold and mesenchymal stem cells, getting the artificial tissue to form meaningful three-dimensional bone has been a major challenge. Problems include difficulties in MSC expansion and decoupling of cell growth and bone matrix formation. A cell line that produces trabecular bone reliably might greatly reduce the second problem, increasing efficiency and reducing dependency on scaffolds.

SUMMARY

A method of producing bone material is provided. The method comprising: culturing CLC3 knockdown osteoblasts ex vivo in culture medium for a length of time such that bone material is produced. In one aspect, the CLC3 knockdown osteoblasts are obtained by culturing CLC3 knockdown mesenchymal stem cells or osteoblast precursor cells in osteoblast differentiation medium for a length of time such that bone material is produced. The material is then either implanted in a patient as bone, or is devitalized to produce bone matrix prior to implantation. The method produces trabecular bone material, which to date has been a substantial challenge. In another aspect, a method is provided of producing a cell able to produce trabecular bone material, comprising knocking down expression of CLC3 in an osteoblast precursor, and differentiating the osteoblast precursor into an osteoblast. In another aspect, a cell culture is provided comprising a CLC3 knockdown mesenchymal stem cell or osteoblast precursor cell, in osteoblast differentiation medium.

BRIEF DESCRIPTION OF THE DRAWINGS

FIG. 1 provides an example of the *Mus musculus* chloride channel protein 3 (CLCN3) mRNA (GenBank: AF029347.1, SEQ ID NO: 1).

FIG. 2 provides primer sequences and predicted PCR products for PCR reactions described in Example 1.

DETAILED DESCRIPTION

Figure 3:
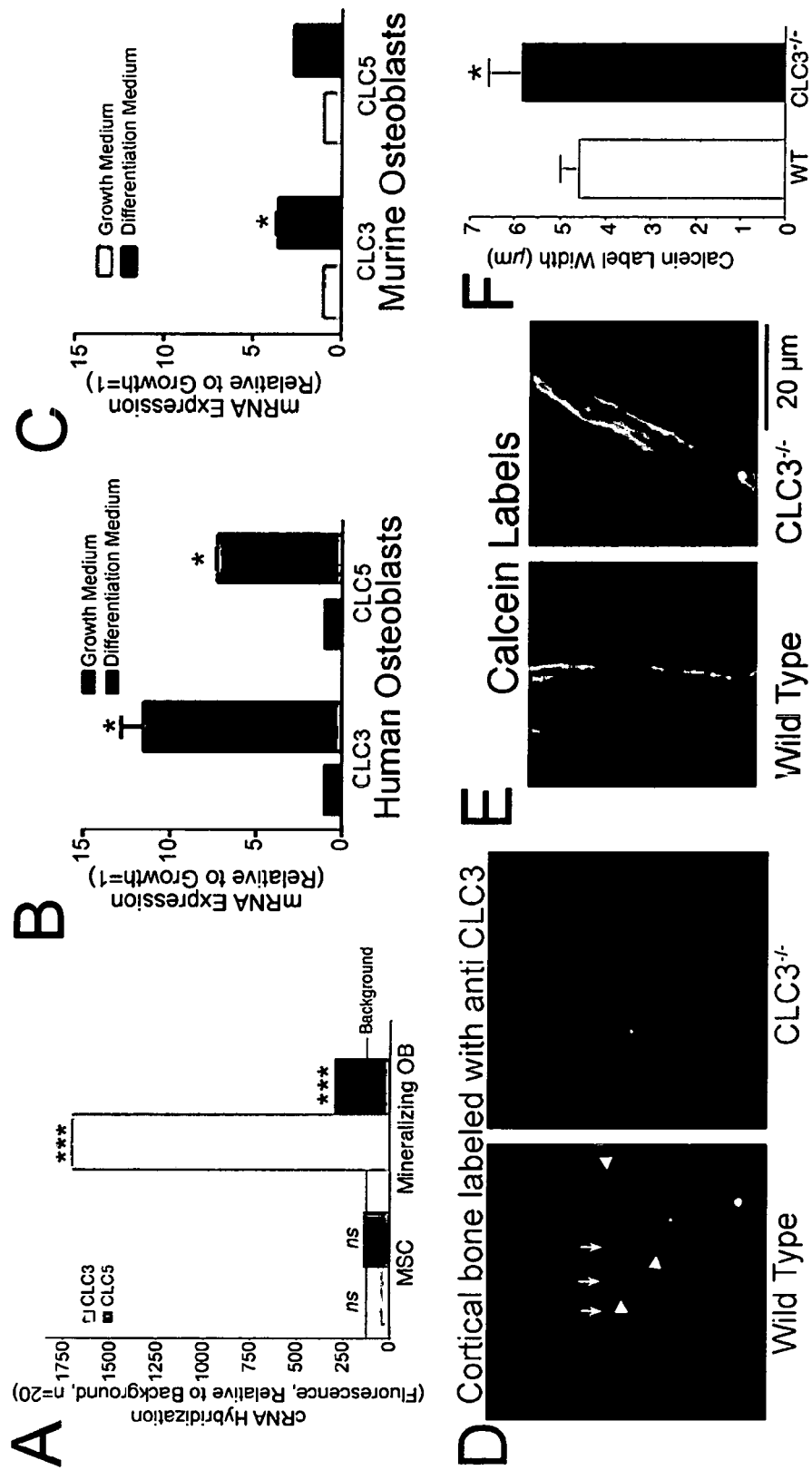
FIG. 3 shows expression of CLC-3 and CLC-5 in mineralizing osteoblasts, and the mild bone phenotype of the CLC-3 knockout mouse. A. Micro-array gene screens of mineralizing osteoblasts showed strong expression of CLC-3 and CLC-5, greatly increased over expression in precursor MSC. The black line labeled background is the median fluorescent signal of non-expressed genes. This is extremely strong expression for this class of genes, in many fold that of cells using CLC-3 in acid vesicles within the cells. B-C. Quantitative PCR confirmed amplification of CLC-3 and CLC-5 in mineralizing human osteoblasts relative to growing cells (B); CLC-3 and CLC-5 mRNAs increased with differentiation. CLC-3 and CLC-5 in murine MSC and osteoblasts (C) showed the same pattern of expression; in this case differences for CLC-5 did not reach significance (p=0.09). In all cases the pattern of CLC expression confirmed gene screening (FIG. 3, A). Larger changes in CLC-5 expression occurred in replicates and in Clcn3−/− osteoblasts (see FIG. 4, F). D. Fluorescent CLC-3 antibody labeling of mouse bone from wild type and CLC-3 knockout animals. Each field is 350 μm across, and shows a section of cortical bone. In the wild type (left) there is strong labeling in the surface layer of osteoblasts at the apical surface (arrows); labeling carries down into the canalicular system connecting the osteocytes and osteoblasts (arrowheads). That the unusual cell membrane pattern is actually CLC-3, and not artifact, is shown by comparison with the CLC-3 knockout bone (right). The weak red at the bone periphery is an artifact due to the edge of the dense matrix. E. Characterization of bone formation in the CLC-3 knockout mouse, in three month old animals labeled with calcein 5 and 1 days before sacrifice, showed only minor effects, including slight broadening of the calcein labels. F. Blinded measurements of inter-label distance showed a small, but significant, increase in the CLC-3 knockout animals. N=20, mean±SEM.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, amelioration of one or more sequelae of an injury or defect, etc.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts. The terms "a" and "an" are intended to refer to one or more.

According to a first aspect of the invention, a method of making bone material, for example trabecular bone or trabecular bone matrix (devitalized bone), e.g., a deposit of a calcium phosphate such as hydroxyapatite having a trabecular three-dimensional structure, is provided. According to one aspect, the bone material produced by the method is useful for implantation to support engraftment of joints and other orthopedic, and reconstructive applications such as titanium rods for teeth. In another aspect, the bone material produced by the method is useful to support healing of nonunion of fractures. In yet another aspect, the bone material produced by the method is useful to support healing of large defects, such as in the skull. The method comprises culturing CLC3 knockdown mesenchymal stem cells in osteoblast differentiation medium for a length of time such that bone material, e.g., trabecular bone material is produced. The method produces CLC3 knockdown osteoblasts. By CLC3 knockdown it is meant that expression of CLC3 in the specified cell is completely reduced or significantly reduced, that is, to the extent that trabecular bone material is made when the CLC3 knockdown mesenchymal stem cells are cultured in osteoblast differentiation medium. Osteoblasts are hydroxyapatite-producing cells, that produce collagen, osteocalcin, and/or osteopontin.

CLC3 is the Chloride Voltage-Gated Channel 3 protein, including the human CLCN3 gene (e.g., as described in HGNC: 2021, Entrez Gene: 1182, Ensembl: ENSG00000109572, OMIM: 600580, UniProtKB: P51790, and GenBank Reference Nos. NM_001243372.1 and NP_001230301.1) or product thereof, and its counterpart in other species, such as the murine CLC3 gene (e.g., as described in Gene ID: 12725, GenBank Reference Nos. NM_007711.3, AF029347 (FIG. 1), and NP_031737.3) described in the Example below.

Cell culture medium includes any useful medium in which cells can be grown in vitro or ex vivo. Non-limiting examples include DMEM, and RPMI (e.g., RMPI 1640, 12% Fetal Bovine Serum and antibiotics). Medium is often supplemented with serum, such as fetal bovine serum, and antibiotics. In the context of the methods of preparing bone described herein, any medium capable of supporting osteoblast cells, and in which hydroxyapatite can be deposited, is suitable.

The CLC3 knockdown cells described herein include mesenchymal stem cells, and mesenchymal cell lines, as well as osteoblast precursor cells or cell lines thereof, in which CLC3 production is knocked down such that when cultured in osteoblast differentiation medium, e.g., as described herein, the cells produce bone. Isolating mesenchymal stem cells from, e.g., bone marrow or adipose tissue is routine. Mesenchymal stem cells can be passaged a number of times to produce useful cell populations. One way to obtain CLC3 knockdown mesenchymal cells is by producing a CLC3 knockdown transgenic mouse, and isolating mesenchymal stem cells from the transgenic animal, as shown below. In that aspect, the animal's cells are used to produce the bone material, which can serve as a useful source of xenogeneic bone matrix. Likewise, in another aspect, the mesenchymal stem cells are human, but not from the individual to be treated, therefore serving as a source of allogeneic bone matrix. In yet another aspect, a patient's mesenchymal stem cells are isolated, and serve as an autologous source of bone or bone matrix.

Mesenchymal stem cells can be differentiated to osteoblasts by a variety of culture methods. In one aspect, they are cultured in osteoblast differentiation medium. By "osteoblast differentiation medium", it is meant cell culture medium suitable for culture of mesenchymal stem cells, and for differentiation of the mesenchymal stem cells to the osteoblast phenotype.

In one aspect, the cell culture medium comprises ascorbic acid and a phosphate source, such as glycerol-2-phosphate, and optionally a glucocorticoid, such as hydrocortisone or dexamethasone. In one aspect, the osteoblast differentiation medium does not include a glucocorticoid. For example, in an example below, osteoblast differentiation was induced by 30 μg/ml ascorbic acid, 200 nM hydrocortisone, and 10 mM glycerol-2-phosphate, with FBS reduced to 10%. Other methods are broadly-known (see, e.g., Apornmaeklong, P, et al., Phenotypic Characterization, Osteoblastic Differentiation, and Bone Regeneration Capacity of Human Embryonic Stem Cell-Derived Mesenchymal Stem Cells 2009 *Stem Cells Dev.* 18(7): 955-968, osteogenic medium was 90% α-MEM, 10% heat-inactivated FBS, 50 μg/mL ascorbic acid, 5 mM β-glycerophosphate, and 100 nM dexamethasone).

As indicated above, the mesenchymal stem cells are CLC3 knockdown cells. A variety of methods of knocking down (e.g., knocking out, reducing, or otherwise lowering) expression of CLC3 are broadly-known and available, and can be implemented readily with knowledge of the gene sequence of CLC3 (e.g. human CLCN3, described above) In one aspect, the method is RNA interference (see examples below), as is broadly-known. Other methods for knocking down gene expression include mutagenesis of the gene, such as mutation of the coding or regulatory sequences of the gene. Additional examples of technologies useful for production of MSCs having expression of CLC3 knocked down include, but are not limited to, shRNA, siRNA, TALEN, or CRISPR/Cas systems.

In one aspect, RNA interference (RNAi) is used. Briefly, RNAi is a process that cells use to 'turn off' or silence unwanted genes. In RNAi, dsRNA (double stranded RNA) in the cell's cytoplasm is cut by an enzyme called Dicer into double stranded small interfering RNA (siRNA) molecules which are 20-25 nucleotides long. This siRNA binds to an RNA-Induced Silencing Complex (RISC) which separates the two strands into the passenger and guide strand. The passenger strand is degraded while the RISC takes the guide strand to a specific mRNA site, cleaving it so that the unwanted target protein is not produced. This is how the gene is 'silenced'. Utilization of endogenous RNAi systems allows for the knockdown of any gene of interest. The RNAi pathway is initiated when dsRNA enters the cytoplasm. The source of the dsRNA may be: synthetic (siRNA) or single stranded RNA (ssRNA) containing two complementary sequences separated by a non-complementary sequence, which folds back on itself to form a synthetic short hairpin RNA (shRNA). siRNA and shRNA are typical methods used for targeted gene knockdown.

As an alternative to gene knockdown, the herein described methods may be achieved through gene knockout, for instance, through TALEN or CRISPR/Cas. Briefly, transcription activator-like effector nucleases (TALENs) are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ, a technique known as genome editing with engineered nucleases. The CRISPR-Cas9 system is composed of a short noncoding guide RNA (gRNA) that has two molecular components: a target-specific CRISPR RNA (crRNA) and an auxiliary trans-activating crRNA (tracrRNA). The gRNA unit guides the Cas9 protein to a specific genomic locus via base pairing between the crRNA sequence and the target sequence. CRISPR loci are composed of a series of repeats separated by segments of exogenous DNA (of ~30 bp in length), called spacers. The repeat-spacer array is transcribed as a long precursor and processed within repeat sequences to generate small crRNAs that specify the target sequences (also known as protospacers) cleaved by Cas9 protein, the nuclease component of CRISPR system. CRISPR spacers are then used to recognize and silence exogenous genetic elements at the DNA level. Essential for cleavage is a three-nucleotide sequence motif (NGG) immediately downstream on the 3' end of the target region, known as the protospacer-adjacent motif (PAM). The PAM is present in the target DNA, but not the crRNA that targets it. Upon binding to the target sequence, the Cas9 protein induces a specific double-strand break. Following DNA cleavage, the break is repaired by cellular repair machinery through non-homologous end joining (NHEJ) or homology-directed repair (HDR) mechanisms. With target specificity defined by a very short RNA-coding region, the CRISPR-Cas9 system greatly simplifies genome editing.

The CLC3 knockdown mesenchymal stem cells are cultured in any bioreactor. A large variety of bioreactor structures and systems are known in the art, and are useful so long as the methods described herein can be performed in the bioreactor. In one aspect, the bioreactor structure in which the bone is formed is shaped to serve as a mold for the produced bone material, as are known in the art. In one aspect, the CLC3 knockdown mesenchymal stem cells are cultured in a hydrogel matrix to facilitate three-dimensional expansion of the trabecular matrix.

In one aspect, the bone matrix described herein is used directly from culture for implantation in a patient. This is especially the case where the mesenchymal stem cells used to prepare the bone material are autologous.

In one aspect, once bone matrix is prepared, it is devitalized, meaning any live cells are killed or removed so that once implanted, the bone material is incorporated into the recipient's tissue and infiltrated by the recipient's cells. Devitalized bone, e.g., bone matrix, is currently prepared by a variety of methods, including by use of formalin and/or other solvents. Other methods of preparing devitalized bone are broadly-known, and are useful for preparing bone matrix from bone produced by the methods described herein.

The decellularized material is optionally sterilized, for example by gamma irradiation. Once decellularized, the bone material is implanted in a patient to support bone growth or repair.

As indicated above, the bone material produced by the method described herein is useful for bone or tooth repair or insufficiency. It can be used as a single piece of material, or it may be comminuted and optionally formed into a slurry prior to implantation, which can be injected. As indicated above, it can be used for bone repair, by placing the material at a site of injury in a patient. It can be used to correct a defect (e.g., a congenital defect) in a patient. It also can be used to treat osteoporosis by introduction of the material at sites of trabecular (cancellous) bone loss, such as the spine, hip, or wrist. In one aspect, the bone material is combined with a metallic, ceramic, or polymeric medical implant device, such as screws, pins, or artificial joint implants or prostheses. The bone material may be grown on, deposited onto or into, or otherwise combined with the medical device. In one aspect, the metal device comprises one or more of a cobalt-chrome alloy, a stainless steel, titanium, tantalum, and/or a titanium alloy that optionally comprises non-metallic and metallic components. In one aspect, the device comprises a commercial pure titanium. In another, the device comprises a titanium alloy that comprises one or more of molybdenum, tantalum, niobium, zirconium, iron, manganese, chromium, cobalt, nickel, aluminum and lanthanum. The titanium alloy may be an alloy comprising Ti, Al, and V, such as, for example, an alloy comprising about 90% wt. Ti, about 6% wt. Al and about 4% wt. V (Ti6Al4V). In one aspect, the device comprises filaments. In another, fused beads. The device may comprise an inorganic, calcium-containing mineral, such as, without limitation, apatite, hydroxyapatite or a mineral comprising Ca, P and O. The scaffold also may comprise a polymer (plastic) and/or a ceramic.

In one aspect, e.g., where the bone material is produced from autologous cells, the bone material is used directly in a patient. In another aspect, where the method produces a bone matrix, once decellularized and optionally sterilized, the bone material according to any aspect of the invention is either used, or packaged into a medically acceptable container, such as a plastic vial or other container, or a pouch, such as barrier-coated or metallized Mylar® or other suitable films, such as polyester terephthalate or polyester films.

Example 1

Osteoblast form an epithelium-like layer with tight junctions separating bone matrix from extracellular fluid. During mineral deposition, calcium and phosphate precipitation in hydroxyapatite liberates 0.8 mole of $H^+$ per mole $Ca^{+2}$. Thus, acid export is needed for mineral formation. Ion transport was examined, supporting osteoblast vectorial mineral deposition. Previously, it was established that Na/H exchangers 1 and 6 are highly expressed at secretory osteoblast basolateral surfaces and neutralize massive acid loads. The Na/H exchanger regulatory factor-1 (NHERF1), a pdz organizing protein, occurs at mineralizing osteoblast basolateral surfaces. It was hypothesized that high capacity proton transport from matrix into osteoblast cytosol must exist to support acid transcytosis for mineral deposition. Gene screening in mineralizing osteoblasts showed dramatic expression of chloride-proton antiporters CLC-3 and CLC-5. Antibody localization showed that CLC-3 and CLC-5 occur at the apical secretory surface facing the bone matrix and in membranes of buried osteocytes. Surprisingly, the $Clcn3^{-/-}$ mouse has only mildly disordered mineralization. However, $Clcn3^{-/-}$ osteoblasts have large compensatory increases in CLC-5 expression. $Clcn3^{-/-}$ osteoblasts in vitro mineralize in a striking and novel trabecular pattern; wild type osteoblasts form bone nodules. In mesenchymal stem cells from $Clcn3^{-/-}$ mice, lentiviral CLC-5 shRNA created $Clcn3^{-/-}$, CLC-5 knockdown cells, validated by Western blot and PCR. Osteoblasts from these cells produced no mineral under conditions where wild type or $Clcn3^{-/-}$ cells mineralize well. Based on this, it is concluded that regulated acid export, mediated by chloride-proton exchange, is essential to drive normal bone mineralization, and that CLC transporters also regulate fine patterning of bone.

Materials and Methods:

Genome-wide expression screening was as described (Robinson et al, 2010, FSH-receptor isoforms and FSH-dependent gene transcription in human monocytes and osteoclasts. Biochem Biophys Res Commun 394: 12-17), using isolated RNA to make double-stranded cDNA, from which biotin labeled cRNA was made and hybridized to the DNA array on glass. The Hu145 133.2 probe-set of 54676 cDNAs, 20 replicates per target, was used (Affymetrix, Santa Clara, Calif.). Presence of transcripts and differences between treatments were determined from the signal and variation of each assay replicate, with statistical confidence indicated. CLC-3 knockout mice. Mice with a knockout allele replacing 13 bp of exon 6 and all of exon 7 with an insert including neomycin resistance were the kind gift of Fred Lamb, Vanderbilt University (Dickerson et al., 2002, Altered GABAergic function accompanies hippocampal degeneration in mice lacking ClC-3 voltage-gated chloride channels. *Brain Res* 958: 227-250). The animals have a mixed 129/Sv and C57Bl/6J background. Knockout, wild type, and heterozygote littermates were used. For analysis of bone growth in situ, animals were labeled with 25 µg/gram body weight with calcein at 4 and 1 day prior to sacrifice, to show bone formation as fluorescent bands in frozen sections of bone as described (Liu et al., 2012, Na+/H+ exchanger regulatory factor 1 (NHERF1) directly regulates osteogenesis. *Journal of Biological Chemistry* 287: 43312-43321).

Human mesenchymal stem cells and osteoblasts. Cells, pre-tested media and supplements (Bullet kit) were from Lonza (Walkersville, Md.). The hMSCs used were from a 22 year old female; human osteoblasts were from an 11 year old female. All Cell culture was at 37° C., in 5% $CO_2$ humidified air, and media were replaced each 2-3 days unless noted. Cells were grown in Dulbecco's modified essential medium (DMEM) with 5.5 mM of glucose with L-glutamine, sodium pyruvate, 10% Fetal Bovine Serum, 30 µg/ml of ascorbic acid, 30 µg/ml gentamicin and 15 ng/ml amphotericin-B.

Mouse MSC were isolated as described (Liu et al., 2012, Na+/H+ exchanger regulatory factor 1 (NHERF1) directly regulates osteogenesis. *Journal of Biological Chemistry* 287: 43312-43321). Bone marrow from six month old mice was collected by flushing femora and tibiae with RPMI 1640, 12% FBS and antibiotics. Disaggregated cells were filtered to remove clumps, and plated. At 3 h nonadherent cells were washed off and re-plated. Cells then adherent on day 2 were washed and grown in mouse MesenCult medium with serum (StemCell Technologies, Vancouver, Canada). At 80% confluence cultures were trypsinized and re-plated at $5 \times 10^5 / cm^2$ and grown in DMEM with 5.5 mM of glucose, FBS, and antibiotics. MSCs were used at passages 5-10. Osteoblast differentiation was induced by 30 µg/ml ascorbic acid, 200 nM hydrocortisone, and 10 mM glycerol-2-phosphate, with FBS reduced to 10%.

Lentivirus. A pLKO shRNA lentiviral plasmid for mouse was purchased as *E. coli* bacterial stock (CLC-N5 TRC shRNA 69494, Sigma, Saint Louis, Mo.), containing the shRNA: CCGGCCTATGATGATTT-CAACACAACTCGAGTTGTGTTGAAATCATCAT-AGGTTTTTG (SEQ ID NO: 2), GFP, puromycin and ampicillin resistance. A colony was isolated and grown in Luria broth with ampicillin; plasmid was isolated by alkaline lysis; endotoxin was removed by nonionic detergent phase separation (MiraCLEAN, Mirus-Bio, Madison, Wis.). Vector preparation and titration were as described (Ravi et al, 2015, Epidermal growth factor activates the Rho GTPase-activating protein (GAP) Deleted in Liver Cancer 1 via focal adhesion kinase and protein phosphatase 2A. J Biol Chem 290: 4149-62; Sena-Esteves et al, 2004, Optimized large-scale production of high titer lentivirus vector pseudotypes. J Virol Methods 122: 131-139; and Geraerts et al, 2005, Upscaling of lentiviral vector production by tangential flow filtration. J Gene Med 7: 1299-1310), and packaged using commercial envelope and packaging plasmid preparations (Addgene, Cambridge, Mass.). High efficiency plasmid delivery was obtained using TransIT-LT1 (Mirus-Bio, Madison, Wis.) in serum-free MEM (OptiMEM, Sigma) with 3 µl of TransIT-LT1 per µg of DNA, incubated with the plasmids for 30 min. This mixture incubated with packaging cells, HEK293T at passage 2-5, in DMEM with 25 mM of glucose and antibiotics, overnight. Medium containing viral particles was collected every 24 h and stored at 4° C., filtered through 0.45 µm cellulose and concentrated with 15 kD retention centrifugal filters (Amicon, Millipore, Billerica, Mass.). Virus titer was determined by anti p24 ELISA (Lenti-X p24 Rapid Titer, Clontech, Mountain View, Calif.).

Viral transduction. Infection was as described (Wein et al, 2008, Lentivirus delivery of shRNA constructs into osteoblasts. Methods Mol Biol 455: 149-155). MSCs were transduced at 60-70% confluence with lentivirus in minimal medium volume 6 µg/ml of 1,5-Dimethyl-1,5-diazaundecamethylene polymethobromide (Polybrene, Sigma). Calculated multiplicity of infection was 9. Cells were placed in growth medium 24 h after the transduction. Cells were selected using 2.5 µg/ml puromycin for 7 days, beginning 48 hours after transduction.

Protein extraction, Western blots, and in situ labeling. $2 \times 10^6$ cells were lysed on ice for 5 minutes with RIPA buffer (10 mM Tris, 1 mM EDTA, 0.5 mM EGTA, 1% Triton X-100, 0.1% sodium deoxycholate, 0.1% SDS, 140 mM NaCl at pH 8, with proteinase and phosphatase inhibitors. Lysates were sonicated and cleared by centrifugation. Protein concentration was determined by bicinchoninic acid (Thermo Fisher) binding. After heating 5 min at 95° C. in sample buffer, aliquots, 40 µg or as stated, were separated on 12% SDS-polyacrylamide gels in Laemmli buffers. Proteins were transferred to polyvinylidine-derivitized nylon; unreacted groups were neutralized in 50 mM Tris, 140 mM NaCl, 0.05% polyoxyethylene-20-sorbitan laurate (Tween 20), pH 7.4 (TBST) with 5% nonfat dry milk overnight at 4° C. Membranes were rinsed with TBST and incubated with primary antibodies: goat polyclonal anti-CLC-5 D-17, recognizing a CLC-5 specific internal epitope (Santa Cruz, Santa Cruz, Calif., USA), 1:150, or rabbit polyclonal anti-CLC-3 raised to amino acids 80-125 of human CLC-3 (Bioss, Woburn Mass., USA), 1:400, or mouse anti-β-actin (Sigma), 1:40,000 overnight at 4° C. Unbound antibody was washed off with TBST; secondary antibodies at were added 1:40,000 for 1 hour: Horseradish peroxidase-conjugated (HRP) goat anti rabbit IgG or HRP donkey anti goat IgG (Jackson ImmunoResearch, Westgrove Pa., USA), or HRP anti mouse IgG (Sigma). After washing, antibodies visualized by enhanced chemiluminescence (SuperSignal, Life Technologies). For in situ labeling of CLC-3/5, protocols used frozen sections of mouse bone and the anti-CLC primary antibodies as in Western blots, and fluorescent second antibodies and photographed in an inverted fluorescence microscope using a 40× oil objective as described (Palagano et al, 2015, Buried in the Middle but Guilty: Intronic Mutations in the TCIRG1 Gene Cause Human Autosomal Recessive Osteopetrosis. J Bone Miner Res 2015 Mar. 31. doi:10.1002/jbmr.2517). Sections of mouse bone fixed with cold acetone, decalcified with 10% sodium citrate; in this case, anti-CLC-3 was used at 1:100 dilution and anti-CLC-5 at 1:25. Secondary antibodies were donkey anti-goat Cy3 and donkey anti-Rabbit Alexa 488, both at 1:500 (Jackson ImmunoResearch, West Grove, Pa. and Invitrogen, Carlsbad, Calif., respectively). Nuclei were stained with Hoechst 33342 (Thermo-Fisher, Pittsburgh Pa.).

RNA and DNA extraction and PCR. Messenger RNA was isolated by oligo (dT) affinity (RNeasy; Qiagen, Valencia Calif., USA). First strand cDNA was synthesized with Moloney murine leukemia virus reverse transcriptase (Superscript III, Life Technologies), and random hexamer primers, 10 mM DTT, and recombinant RNase inhibitor (RNase-OUT, Life Technologies). Quantitative RT-PCR was performed using cDNA as the template in 25 µl reaction mixtures with premixed SYBR green, dNTPs, buffer, Taq DNA polymerase (SYBR Green Master Mix; Stratagene/Agilent, Santa Clara, Calif. USA) with 1 µl of first strand cDNA and 250 nM primers (FIG. 2). Expression relative to mouse β-actin or human glyceraldehyde-3-phosphate dehydrogenase cDNA was calculated as described (Robinson et al., 2009, Estrogen inhibits RANKL-stimulated osteoclastic differentiation of human monocytes through estrogen and RANKL-regulated interaction of estrogen receptor-alpha with BCAR1 and Traf6. *Exp Cell Res* 315: 1287-1301). Product sizes were verified by electrophoresis on 2% agarose. Unless noted, PCR used 94° C. denaturation for 2 minutes, 57° C. annealing for 30 seconds, and 72° C. elongation for 1 minute, for 36 cycles, and duplicate assays each run in duplicate were performed. DNA was isolated by homogenization in denaturing buffer and binding on silica glass columns (EZNA DNA/RNA Isolation, Omega BioTek, Norcross, Ga.). PCRs contained 1 µl of DNA and 0.5 unit of Taq polymerase (Platinium Taq, Invitrogen, Carlsbad, Calif., USA).

Histomorphometry, histochemistry and in situ labeling. Alkaline phosphatase activity was determined using 7-bromo-3-hydroxy-2-naphthoic-o-anisidide (naphthol AS-BI phosphate) substrate, reacted with fast blue to produce blue insoluble product, at pH 9.5 (leukocytes alkaline phosphatase kit, Sigma). Von Kossa silver stain for mineral used cell cultures fixed in 3.7% formaldehyde for 2 minutes. Mineral was stained with 2% AgNO3 under UV light for 10 minutes. Animals were labeled with 25 µg/g of animal weight of calcein 4 days and 1 day prior to sacrifice. Frozen sections of vertebrae, 4 µm thick, were obtained using carbide blades and a tape transfer system (CryoJane; Instrumedics, St. Louis, Mo.). Histomorphometric analysis was as described (Robinson et al., 2012, Gene disruption of the calcium channel Orai1 results in inhibition of osteoclast and osteoblast differentiation and impairs skeletal development. *Laboratory Investigation* 92: 1071-1083).

Statistics. Unless stated, the data are mean±SD. Individual comparisons used Student's T test; Multiple comparisons used analysis of variance; $p \leq 0.05$ is reported as significant.

Results:

The chloride/hydrogen exchanger CLC-3 is very strongly expressed in mineralizing osteoblasts; CLC-5 occurs at significant levels. It was previously discovered that NHE1 and NHE6 as massively expressed sodium-hydrogen exchangers in the basolateral surface of mineralizing osteoblasts (Liu et al., 2011, High capacity Na+/H+ exchange activity in mineralizing osteoblasts. *Journal of Cell Physiology* 226: 1702-1712). Those cells form the epithelium-like boundary on the osteon; only this surface is exposed for release and efflux of protons to the extracellular compartment (Liu et al., 2012, Na+/H+ exchanger regulatory factor 1 (NHERF1) directly regulates osteogenesis. *Journal of Biological Chemistry* 287: 43312-43321). The other surface of the osteoblasts, the apical membrane, abuts the bone matrix compartment. It is hypothesized that it must support equal and regulated H+ influx from matrix into the osteoblast.

Using Affymetrix cRNA microarrays (Robinson et al., 2010, FSH-receptor isoforms and FSH-dependent gene transcription in human monocytes and osteoclasts. *Biochem Biophys Res Commun* 394: 12-17) expression was compared for undifferentiated human MSC and osteoblasts (FIG. 3, A). In the human cells, there was a striking change of CLC-3 expression in MSC, with a median signal in MSC of 29 with p value for expression from 0.12-0.35, to a median signal in mineralizing osteoblasts of 1,800 with p values uniformly <0.0002. A second CLC, CLC-5, was also increased in mineralizing osteoblasts, but at lower levels, but with convincing p values of 0.002 to 0.004. The same gene screens revealed the increases in NHE1 and NHE6 to about 1000 with p values of <0.0002 in osteoblasts, previously reported (Liu et al., 2011, High capacity Na+/H+ exchange activity in mineralizing osteoblasts. *Journal of Cell Physiology* 226: 1702-1712; Liu et al., 2012, Na+/H+ exchanger regulatory factor 1 (NHERF1) directly regulates osteogenesis. *Journal of Biological Chemistry* 287: 43312-43321). Other CLCs and other potential regulated inward proton transporters were not strongly expressed in human osteoblasts (not illustrated). It was therefore concluded that expression of CLC-3 and CLC-5, together with NHE1 and NHE6 at the basolateral membrane, might form the basis of a coordinated transcellular system to move H+ produced by precipitation of hydroxyapatite in the matrix. This approach assumes that the major mechanisms have a strong overlap in humans and mice used in subsequent work; this assumption was validated by PCR assays comparing the species (FIG. 3, B-C). In both human and murine osteoblasts CLC-3 and CLC-5 mRNAs both CLCs were increased in mineralizing cells. Subsequently studied in murine MSC and osteoblasts.

This was followed by in situ antibody labeling of CLC-3 in bone from Clcn3$^{+/+}$ and Clcn3$^{-/-}$ mice (FIG. 3, D). The CLC-3 labeling consistent with osteoblast membrane expression of CLC-3 in surface osteoblasts and in the membranes of the canalicular system. Osteocytes buried in mineral, from earlier layers of bone formation, maintain processes in these canaliculi, connecting to the surface layer of osteoblasts synthesizing new matrix. In bone from Clcn3$^{-/-}$ animals labeling was absent (FIG. 3, D, right), demonstrating that the strong CLC-3 labeling in the wild type animal bone is not an artifact.

Surprisingly, the bone phenotype of Clcn3$^{-/-}$ animals, at least at the three month's age studied, was very mild. By visual inspection the bones of each animal appeared unremarkable and very similar; micro-computed tomography showed differences on the order of 5%, with a trend to lower bone volume, trabecular thickness, and increased trabecular spacing in the Clcn3$^{-/-}$ relative to wild type animals, but none of these reached significance (n=8, not illustrated). Bone formation in Clcn3$^{+/+}$ and Clcn3$^{-/-}$ animals was compared directly using calcein labeling of mineral deposition in vivo (FIG. 3, E-F). Blinded measurement of calcein double labels, done 5 and 1 days before sacrifice, showed that the Clcn3$^{-/-}$ mice have anomalous bone mineral deposition, limited to blurring of mineral deposition. Note that broadened calcein lines reflect delayed mineralization rather than increased mineralization; nonmineralized matrix accumulates in bone mineralization defects including vitamin D deficiency. It was hypothesized that the mild phenotype reflects that CLC-5 might compensate for CLC-3 loss.

Figure 4:
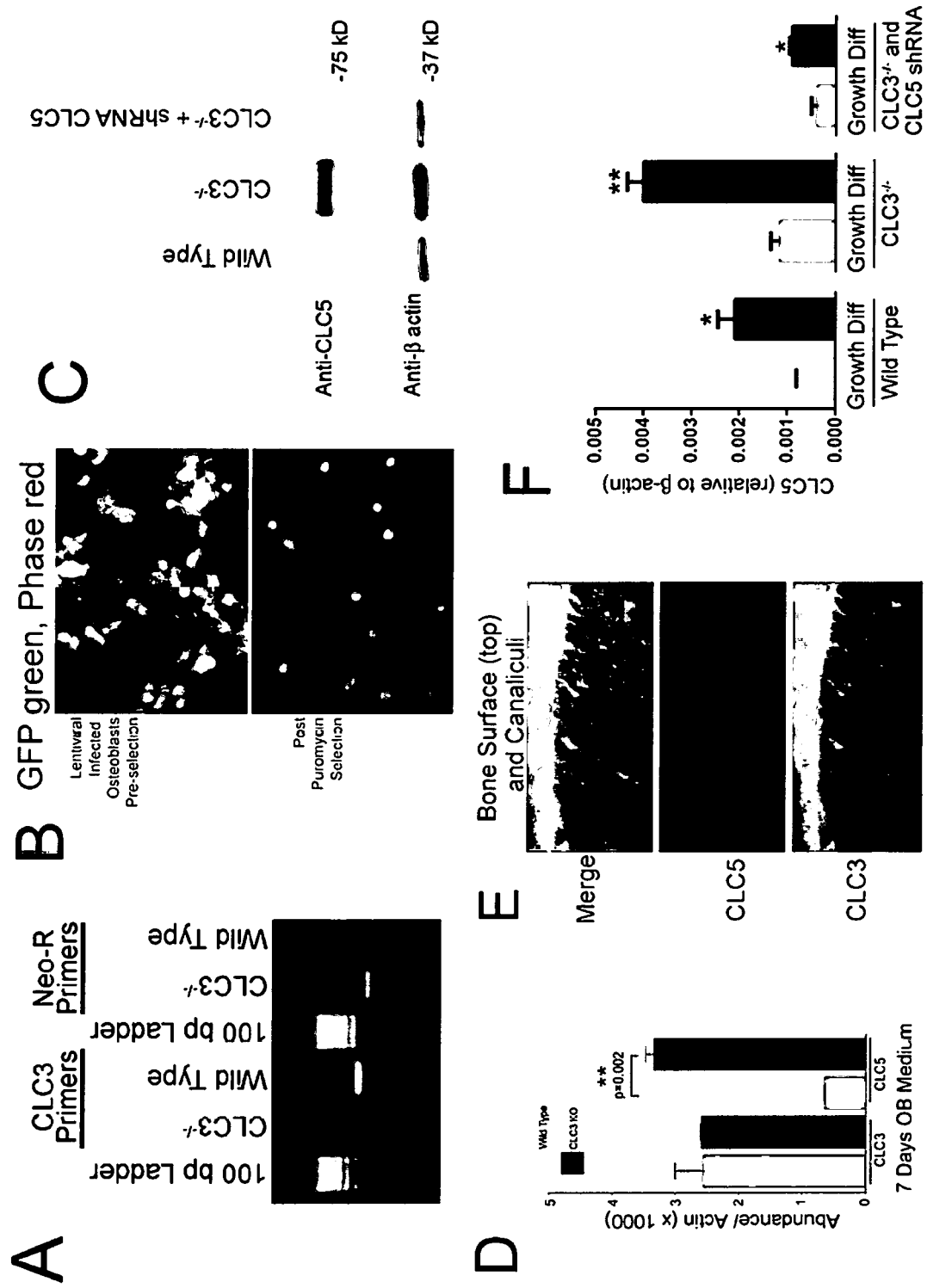
FIG. 4 shows preparation of CLC-3 and CLC-3/5 null mesenchymal stem cells. A. PCR to probes in exon 6 to 7 showing complete removal in MSC from CLC-3 knockout animals. The neomycin control verifies presence of the insert (see text). B. Green fluorescent protein to document lentiviral infection of MSC with plasmid carrying both GFP and CLC-5 shRNA. Initial infection was ~25% efficient; puromycin selection increased the proportion of knockdown cells to quantitative (lower panel). However, shRNA degradation of target was ~80% efficient, see PCR data following. C. Western blot of CLC-5 wild type and Clcn3−/− MSC, with and without lentiviral knockdown of CLC-5, in osteoblast differentiation medium 2 weeks. The increase in CLC-5 in the CLC-3 null cells is not an artifact, see PCR assays following. With lentiviral shRNA, CLC-5 protein declined 80-90% relative to matched cultures without shRNA, to levels similar to wild type CLC-5 expression (left). One of two Western blots with similar results is shown. D. Effect of CLC-3 KO on CLC-3 and CLC-5 mRNA expression. For CLC-3, primers for exons 1-2 detect a region unaffected by the knockout (in which a portion of exon 6 and exon 7 are deleted); this shows the amount of non-functional CLC-3 mRNA, which is not changed significantly in the knockout. The probe for CLC-5 amplifies a portion of exon 7; note the increase in CLC-3 knockout cells. The primers are listed in FIG. 2. Mean±range, n=2 is shown, in one of two experiments with similar results. E. Antibodies demonstrate that CLC-3 and CLC-5 occur in wild-type murine bone in essentially the same distribution, in the canalicular system and at the basolateral surface of the osteoblasts. High power fields, 400 microns across. Distribution of CLC-3 is shown in green, CLC-5 in red, and the two merged are shown at the top. F. Effect of lentiviral shRNA on CLC-5 in wild type littermate and CLC-5 knockout MSC, in growth medium (left of each group) and after one week in differentiation medium. Differences relative to the growth medium controls, p<0.05, *, of p<0.01. One of two experiments is shown, each with n=2.

CLC-3 knockout osteoblasts have greatly increased CLC-5 expression. Not having access to CLC-5 animals, study of bone formation by MSCs in culture was undertaken. The MSCs from CLC-3 animals could then be treated with lentivirus shRNA to reduce CLC-5, to determine the effect of low expression of both CLCs on mineral deposition in culture. This might be necessary in any case, since if the function of CLCs is essential, the bone defect of CLC-3 and CLC-5 absence might lethal. To confirm the genotype of MSCs from CLC-3 mice, the KO and wild type (WT) alleles of CLC-3 were identified by PCR with genomic DNA using primers showing that the targeted region in exons 6-7 was absent in cell cultured from the knockout mice (FIG. 4, A), with targeting insert neomycin resistance shown as a positive control. Western blotting revealed low levels of CLC-3 protein in Clcn3$^{-/-}$ mouse (not shown); defective protein is present, but non-functional (Dickerson et al., 2002, Altered GABAergic function accompanies hippocampal degeneration in mice lacking ClC-3 voltage-gated chloride channels. *Brain Res* 958: 227-250). A plasmid with shRNA targeting CLC-5, containing a green fluorescent protein insert, puromycin and ampicillin resistance, and packaged it in lentiviral particles was obtained. Lentiviral infection was monitored by GFP fluorescence (FIG. 4, B). After initial infection, 25% of cells had GFP; after puromycin selection and two weeks in culture, all cells were GFP positive (FIG. 4, B, lower panel). In wild Type MSCs, CLC-5 was present at low levels (FIG. 4, C, left). However, in osteoblasts from Clcn3$^{-/-}$ animals, CLC-5 protein was greatly increased by an unknown mechanism (FIG. 4, C, middle). After infection with the viral vector CLC-5 protein expression was suppressed by shRNA. This was not complete, but to levels similar to CLC-5 in wild type cells (FIG. 4, C, right). These results were consistent with quantitative PCR in osteoblasts cultured for one week in osteoblast differentiation medium (FIG. 4, D). Wild type controls infected with scrambled shRNA showed no difference relative to the uninfected wild type (not illustrated). That CLC-5 mRNA and protein is greatly amplified in Clcn3$^{-/-}$ animals, which have a near normal bone phenotype (FIG. 3, E-F) suggested that CLC-5 might functionally compensate for CLC-3 loss. If this hypothesis is correct, CLC-5 and CLC-3 should occur in similar distribution in osteoblasts and osteocytes. This was the case, with antibody labeling of CLC-3 and CLC-5 in bone of normal animals having and overlapping distribution (FIG. 4, E). Thus, in the osteon, the two channels are co-distributed and might compensate each other to a significant extent. Additional studies of CLC-5 mRNA in wild type and Clcn3$^{-/-}$ cells, in growth medium and in differentiation medium, with and without lentiviral CLC-5 shRNA confirmed greatly increased CLC-5 in Clcn3$^{-/-}$ cells, and that the shRNA reduced CLC-5 by about 80% in either cell type (FIG. 4, F). C57 black mouse cells and wild type CLC-3$^{+/+}$ cells, mainly 129/Sv, showed the same pattern of CLC-3 and CLC-5 expression, with or without lentiviral CLC-5 knockdown, indicating that there is probably not a strong strain-specific effect on CLC expression in mice (not shown). The reason for the residual CLC-5 is uncertain, but likely is due to insufficient hsRNA to suppress the very strong CLC-5 expression. Next bone formation was studied in Clcn3-/- cells with and without CLC-5 hsRNA relative to bone formation in wild type cells.

Figure 5:
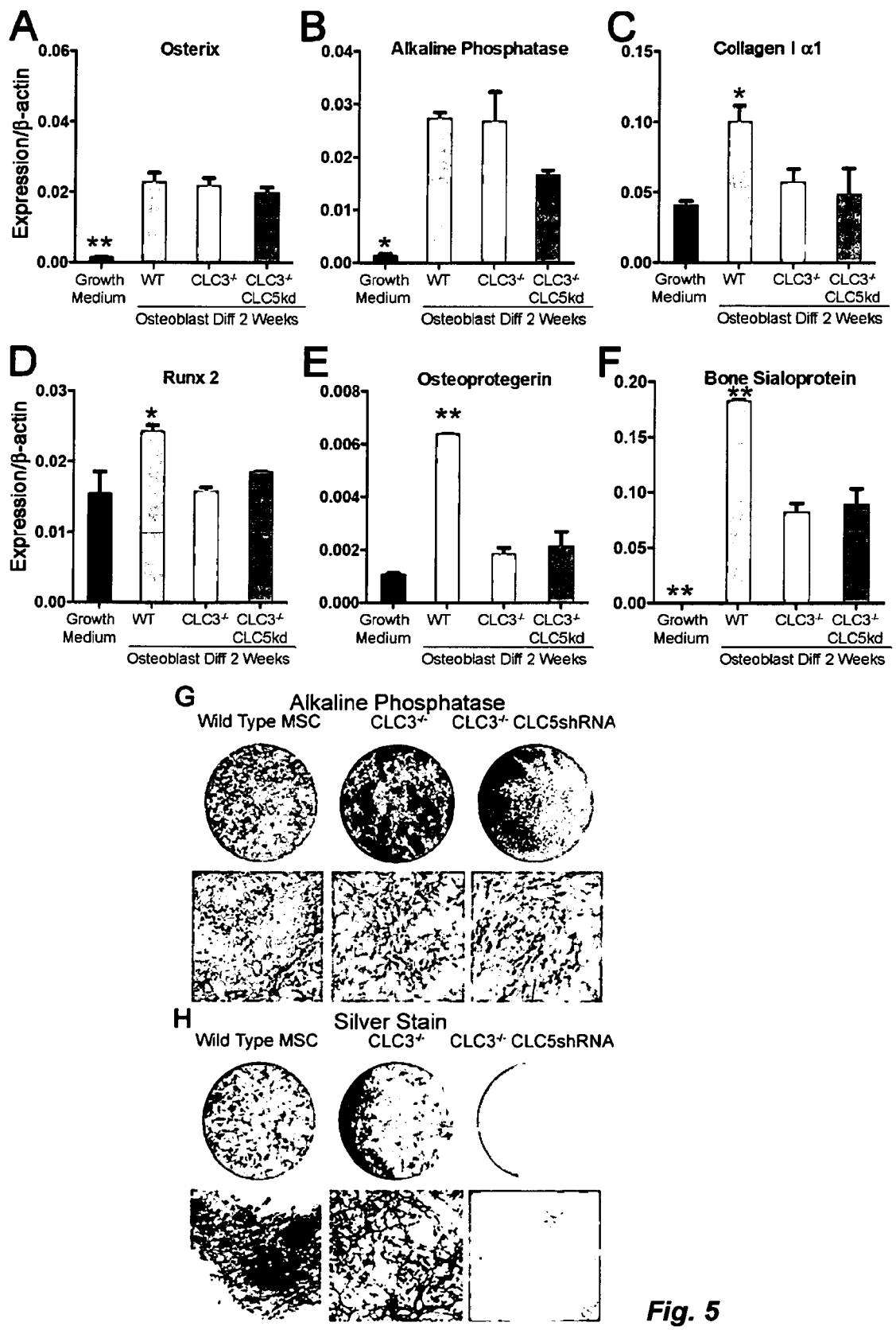
FIG. 5 shows the effect of CLC-3 absence, and of CLC-5 knockdown in Clcn3−/− cells, on bone matrix production and mineralization. A-F. Quantitative PCR for major osteoblast proteins in growing wild type cells and in wild type, Clcn3−/− cells, and Clcn3−/− cells with lentiviral CLC-5 shRNA, at two weeks in osteoblast differentiation medium. A. Osterix. B. Alkaline phosphatase. C. Col I α1. D. Runx2. E. Osteoprotegerin. F. Bone sialoprotein. The proteins are expressed less in growing cells, and highest in wild type. In some, but not all, cases, expression is reduced in the knockout/knockdown cells, but remains higher than in the growing cells. G-H. Alkaline phosphatase and mineral production in cell cultures. Round fields are whole wells of 6 well plates; micrographs are 1.6 mm across. G. Alkaline phosphatase activity was similar in wild type cells or Clcn3−/− cells with and without CLC-5 shRNA. Alkaline phosphatase distribution was more uniform in Clcn3−/− ±CLC-5 knockdown cells. The lower panels are low power micrographs in cultures 14 days in osteoblast differentiation medium. H. In whole cultures, mineral appeared nodular in the control, was more uniformly distributed in Clcn3−/−, cells, and was absent in the Clcn3−/− cells with CLC-5 shRNA at 14 days in osteoblast differentiation medium. Low power micrographs showed that the Clcn3−/− cells had a remarkable trabecular pattern (see FIG. 6). This pattern of bone differentiation was remarkably consistent in different isolates of Clcn3−/− cells, in two MSC isolates and in several replicates of each isolate.

Effect of eliminating CLC-3 and suppressing CLC-5 on bone formation in vitro. To understand the importance of increased CLC-5 expression in MSC cultured from CLC-3 mice shRNA via lentivirus infection was applied to reduce CLC-5 expression in bone-forming cultures from Clcn3$^{-/-}$ mice, and characterized the resulting bone differentiation. The pre-tested shRNA-GFP-puromycin resistance construct was designed to target mouse CLC-5, and showed specific protein suppression during differentiation in the mouse osteoblast cultures (FIG. 4, F). Retention of 10-20% of the very high CLC-5 expression reflects a common effect with highly expressed genes, where a large amount of mRNA production and processing overwhelms the dicer system's ability to degrade shRNA complexes, just as occurs in overwhelming viral infections. Notwithstanding that CLC-5 suppression was imperfect, the method made cells with suppressed CLC-5 similar to levels in wild type cells, which was then hypothesized would significantly affect bone differentiation in CLC-3 negative, CLC-5 knockdown cells on osteoblast differentiation. Analysis of bone-related mRNAs showed that expression is, as expected, increased by differentiation in osteoblast-promoting medium. Bone protein and promoter expression was highest in wild type cells (FIG. 5, A-F). For the bone transcription factor osterix, expression was invariant with CLC-3/5 status; the transcription factor RunX2 was highest in wild type cells Alkaline phosphatase, osteoprotegerin, and bone sialoprotein were significantly increased over growing cells in wild type and CLC-3/5 modified cells, but were mostly highest in the wild type. This may reflect in part different time courses of production in the different cell types: Alkaline phosphatase, a durable ectoenzyme had strong and uniform activity at two weeks (FIG. 5, G) in wild type and CLC modified cells. Type I collagen was highly expressed including in all of the cell types; in any osteoblast culture a minority of cells are active in bone formation; relatively highly expressed proteins are less specific markers for that reason.

In contrast, by undertaking careful analysis of mineralization in culture, a remarkable aspect of mineralization in Clcn3$^{-/-}$ cells was uncovered, possibly due to the increased CLC-5 expression in these cells (FIG. 4). Specifically, mineral production was widespread and occurred in a distinct, fine trabecular pattern with sharp boundaries (FIG. 5, H, bottom middle panel). In spite of many attempts to formulate trabecular bone bioreactors, mineralization always has been in patchy, round or spherical nodules and bone produced is not generally useful for implantation. The highly branching trabeculae were a characteristic of the cells from CLC-3 mice and might indicate a practical method of creating trabecular bone in vitro; it occurred uniformly in CLC-3 cells from separate MSC isolations and in over a dozen separate tissue culture differentiation assays. In bone differentiation in vitro, mineralization has been inconsistent, unreliable (Jakob et al., 2012, Perspective on the evolution of cell-based bone tissue engineering strategies. *Eur Surg Res* 49: 1-7), and typically unimpressive even when best results are shown. Importantly, in keeping with the hypothesis that Cl/H exchange supports mineral deposition, mineral was uniformly absent in matched two week cultures of Clcn3$^{-/-}$ cells with CLC-5 shRNA.

Figure 6:
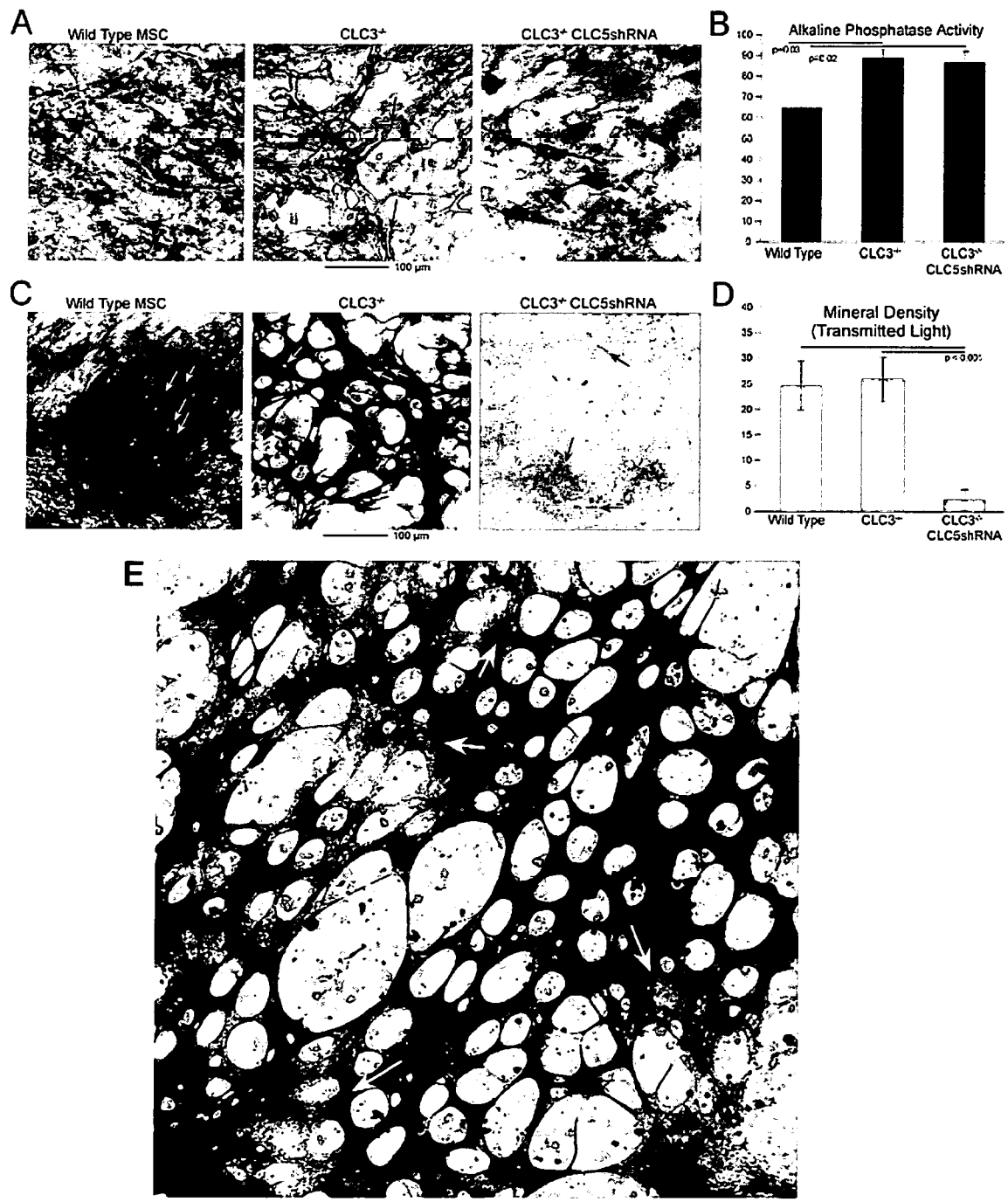
FIG. 6 shows the characteristics of alkaline phosphatase and mineral deposition at high power in wild type, Clcn3−/−, and Clcn3−/− with CLC-5 shRNA cells. All data for cultures are at two weeks in bone differentiation medium, except part G. A. Alkaline phosphatase. Strong alkaline phosphatase activity occurs in fine linear areas consistent with cell surface and cell process-associated activity in wild type (left), Clcn3−/− (middle) and Clcn3−/− and CLC-5 shRNA cells (right). In Clcn3−/− cells there is dense alkaline phosphatase adjacent to much of the trabecular bone (refractile, unstained) (arrows, center panel). Fields are 250 μm across. B. Quantitative alkaline phosphatase activity at three weeks by densitometry of four replicates, similar to FIG. 5, G-H upper panels. There was no difference between CLC-3 negative and CLC-3 negative CLC-5 shRNA cells. C. Silver stain for bone mineral. In wild type and in Clcn3−/− cells, lacunae indicate that cells incorporated in the matrix. In the Clcn3−/− and CLC-5 shRNA cells, no significant mineral occurs, although minor amounts of linear labeling are seen in the pattern similar to strong cell surface associated alkaline phosphatase activity (A, right panel, arrows), suggesting non-specific phosphate precipitation at sites of very high alkaline phosphatase (see text). Fields are 250 μm across. D. Densitometry for mineral, quantified as dark matter in transmitted light, in four replicates of the three cell types at two weeks in differentiation medium. There was no difference in overall absorbance in wild type and Clcn3−/− cells, despite the remarkable difference in matrix pattern. The Clcn3−/− and CLC-5 shRNA cells made no meaningful mineral. E. A cell culture of Clcn3−/− cells as in (D) middle, but maintained in osteogenic medium for an additional week. The mineral area has expanded and now appears in sheet-like form with windows in irregular distribution. In this large area, it is clearly seen that some of the pattern is laid out but not fully mineralized. Magnification is the same as (D), with an expanded field, 750 µm across.

Properties of bone matrix in CLC defective cells at high resolution. Because of the remarkable trabecular nature of mineralization by the CLC-3 cultured MSCs these cultures were examined at high magnification and quantified alkaline phosphatase activity and mineral density. In all cell types, alkaline phosphatase occurred in fine linear patterns consistent with cell surface-associated activity (FIG. 6, A), in keeping with its cell surface expression as established in other contexts (Magnusson et al., 1999, Isoforms of bone alkaline phosphatase: characterization and origin in human trabecular and cortical bone. *J Bone Miner Res* 14: 1926-1933). In the Clcn3$^{-/-}$ cells dense alkaline phosphatase activity occurred adjacent the trabecular bone, in keeping with its distribution at the bone-attached osteoblast surface in vivo (FIG. 6, A, middle, arrows). Quantitative alkaline phosphatase activity showed minor increases in activity in the cells with modified CLCs, but no difference between Clcn3$^{-/-}$ and Clcn3$^{-/-}$, CLC-5 shRNA (FIG. 6, B).

Silver stain for bone mineral was strongly positive in wild type and CLC-3 cells. At high power, gaps in the mineral were observed consistent with bodies of cells becoming osteocytes that are incorporated in the mineralized matrix (FIG. 6, C, left and middle panels). In Clcn3$^{-/-}$, CLC-5 shRNA cells, no significant mineral as deposited. There were minor amounts of linear labeling at high power, in the morphology associated with the cell surface. This most likely reflects that, in the presence of the glycerol-2-phosphate substrate at high concentration (10 mM), some calcium-phosphate precipitate occurs outside of cellular mineral transport, similar to calcification of hypertrophic cartilage. Overall mineral deposition in wild type and Clcn3$^{-/-}$ cells was essentially the same at two weeks, notwithstanding the profound difference in the pattern of mineralized matrix. The Clcn3$^{-/-}$, CLC-5 shRNA cells made no significant mineral. Following the mineralization in Clcn3$^{-/-}$ cells for an additional week extended the mineral deposition to a sheet-like morphology with windows (FIG. 6, E), and it was clear that the fine patterning boundaries for bone formation were defined before mineralization was complete (Arrows, FIG. 6, E).

Example 2

Chloride-Hydrogen Antiports CLC3 and CLC5 Drive Osteoblast Mineralization and Regulate Fine-Structure Bone Patterning In Vitro Ion transport supporting vectorial mineral deposition in osteoblasts was examined. An epithelium-like layer of osteoblasts separates, by tight junctions, bone matrix from extracellular fluid. In mineral deposition, calcium and phosphate in solution liberate ~0.8 Er/mole of calcium precipitated. Thus, acid export can drive mineral formation. Previously, massive expression of Na$^+$/H$^+$ exchangers 1 and 6 (NHE1/6) at the basolateral surface of secretory osteoblasts was identified. Further, the pdz organizing protein, Na$^+$/H$^+$ exchange regulatory factor 1 (NHERF1), occurs in mineralizing osteoblast basolateral surfaces. NHERF1 is essential to normal osteoblast function, including for phosphate transport via the neutral phosphate transporter-2 (Npt2). It was hypothesized that high-capacity proton transport from matrix to osteoblasts at the apical surface also must exist to support mineral deposition.

Materials and Methods:

CLC3 knockout mice. Mice with part of ClCN3 exon 6, and all of exon 7, replaced were the kind gift of Fred Lamb, Vanderbilt University (Dickerson et al., Lamb FS. Altered GABAergic function accompanies hippocampal degeneration in mice lacking ClC-3 voltage-gated chloride channels. *Brain Res.* 2002 Dec. 27; 958(2):227-50). The animals have a mixed 129/Sv and C57Bl/6J background. Knockout, wild type, and heterozygote littermates were used.

Mesenchymal stem cells. All Cell culture was at 37° C., in 5% CO$_2$ humidified air, and media were replaced each 2-3 days unless noted. Bone marrow from six month old mice was collected by flushing femora and tibiae with RPMI 1640, 12% FBS and antibiotics. Disaggregated cells were filtered to remove clumps, and plated. At 3 h nonadherent cells were washed off and re-plated. Cells then adherent on day 2 were washed and grown in mouse MesenCult medium with serum (StemCell Technologies, Vancouver, Canada). At 80% confluence cultures were trypsinized and re-plated at 5×10$^5$/cm$^2$. MSCs were used at passages 5-10. Differentiation used DMEM with 5.5 mM glucose, 10% FBS, gentamicin and amphotericin-B. Osteoblastic differentiation was induced by adding 3 0 µg/ml ascorbic acid, 200 nM hydrocortisone, and 10 mM glycerol-2-phosphate.

Lentivirus. HEK293T cells from passage 2 to 5, were grown in DMEM with 25 mM of glucose, 12% FBS, 30 mg/ml gentamicin and 15 ng/ml amphotericin-B. During the lentiviral production serum-free media (OptiMEM-I, GIBCO-Life Technologies, Grand Island, N.Y., USA) was used. A pretested mouse CLC5 shRNA (ClCN5 Mission TRC shRNA, TRCN0000069494, Sigma, St Louis, Mo. USA) sequence CCGGCCTATGATGATTT-CAACACAACTCGAGTTGTGTTGAAATCATCAT-AGGTTT TTG (SEQ ID NO: 2), was used. The ClCN5 Mission TRC shRNA plasmid contains ampicillin and puromycin resistance. A bacterial glycerol stock was grown on LB agar with 50 µg/ml ampicillin, colonies were picked and grown in LB broth and DNA was extracted by alkaline lysis and purified. To remove bacterial endotoxins a MiraCLEAN Endotoxin Removal (MirusBio) was used. DNA was determined and plasmid was sequenced verify identity to the published sequence. Vectors were produced by transfection into HEK293T; 5×10$^6$ cells were seeded in 10 cm dishes 24 h prior to transfection in growth medium. Medium was changed 2 h prior to transfection with OptiMEM. For transfection, 5.7 µg of plasmid DNA was used per dish, with 0.5 µg of envelope plasmid pMD2G, 2.6 µg of packaging plasmid (1.3 µg of pRSV-rev plus 1.3 µg of pMDL/pRRE), from Addgene, Cambridge Mass., and 2.6 µg of vector plasmid (ClCN5, Sigma, see above). For high efficiency plasmid DNA delivery, a transfection reagent (TransIT-LT1, Mirus Bio, Madison Wis., USA) was diluted in OptiMEM with 3 µl of TransIT-LT1 per µg of DNA, and incubated with plasmids for 30 min. The mixture was added to the packaging cells and incubated overnight. The medium was replaced with OptiMEM every 24 h for 3 days post infection. Conditioned media, with viral particles, were saved and stored at 4° C. Conditioned media were sterilized by 0.22 µm cellulose filters and collected by ultra-filtration in spin filters (Amicon Ultra-15, Millipore, Billerica Mass., USA). Virus titer was determined by ELISA (Lenti-X p24 Rapid Titer, Clontech/Takara, Mtn View, Calif., USA).

Transduction of MSCs. WT and KO MSCs were seeded at 80-90% confluence to infect 10$^5$ cells per well in six-well plates in Polybrene (4 µg/ml, Sigma). The medium was changed to growth medium 16 h after addition of lentivirus. 72 h post-infection puromycin selection was initiated.

Protein extraction, Western blots, and in situ labeling. Two×10$^6$ cells were lysed on ice for 5 minutes with RIPA buffer (10 mM Tris, 1 mM EDTA, 0.5 mM EGTA, 1% Triton X-100, 0.1% sodium deoxycholate, 0.1% SDS, 140 mM NaCl at pH 8, with proteinase and phosphatase inhibitors. Lysates were sonicated 5 minutes at intervals to avoid overheating, cleared by centrifugation at 6,000×g for 15 minutes. Proteins were determined by dye binding (BCA, Life Technologies). After heating 5 min at 95° C. in sample buffer, aliquots, 40 µg or as stated, were separated on 12% SDS-polyacrylamide gels in Laemmli buffers. Proteins were transferred to polyvinylidine-derivitized nylon; unreacted groups were neutralized in 50 mM Tris, 140 mM NaCl, 0.05% polyoxyethylene-20-sorbitan monolaurate (TBST) with 5% nonfat dry milk overnight at 4° C. Membranes were rinsed with TBST and incubated with primary antibodies: goat polyclonal anti-ClC5 D-17, recognizing a CLC5 specific internal epitope (Santa Cruz, Santa Cruz, Calif., USA), 1:150, rabbit polyclonal anti-ClC3 raised to amino acids 80-125 of human CLC3 (Bioss, Woburn Mass., USA), 1:400, or mouse anti-#-actin (Sigma), 1:40,000 overnight at 4° C. Unbound antibody was washed off with TBST, and secondary antibodies at were added 1:40,000 for 1 hour: Horseradish peroxidase-conjugated (HRP) goat anti rabbit IgG or HRP donkey anti goat IgG (Jackson ImmunoResearch, Westgrove Pa., USA), or HRP anti mouse IgG (Sigma). After washing, antibodies visualized by enhanced chemiluminescence (SuperSignal, Life Technologies). For in situ labeling of CLC3/5, protocols used frozen sections of mouse bone and the anti-CLC primary antibodies as in Western blots, but fluorescent second antibodies as described (Liu et al., High capacity Na+/H+ exchange activity in mineralizing osteoblasts. *J Cell Physiol.* 2011 June; 226(6):1702-12).

RNA extraction and quantitative PCR. Messenger RNA was isolated by oligo (dT) affinity (RNeasy; Qiagen, Valencia Calif., USA). First strand cDNA was synthesized by reverse transcriptase (Superscript III, Life Technologies), with random hexamer primers, 10 mM DTT, and recombinant RNase inhibitor (RNaseOUT, Life Technologies). Quantitative RT-PCR was performed using cDNA as the template in 20 µl reaction mixtures with premixed SYBR green, dNTPs, buffer, Taq DNA polymerase (SYBR Green Master Mix; Stratagene/Agilent, Santa Clara, Calif. USA) and 20 ng primer pairs for each cDNA (see FIG. 2). Expression relative to #-actin cDNA was calculated, and product size was verified by electrophoresis on 2% agarose essentially as described (Robinson et al., Estrogen inhibits RANKL-stimulated osteoclastic differentiation of human monocytes through estrogen and RANKL-regulated interaction of estrogen receptor-alpha with BCAR1 and Traf6. *Exp Cell Res.* 2009 Apr. 15; 315(7):1287-301).

Histochemistry. ALP activity was determined using 7-bromo-3-hydroxy-2-naphthoic-o-anisidide (naphthol AS-BI phosphate) as substrate, and fast blue to precipitate reacted substrate as a blue insoluble product, at pH 9.5 (leukocytes alkaline phosphatase kit, Sigma). Von Kossa silver stain for mineral used cell cultures fixed in 3.7% formaldehyde for 2 minutes. Mineral was stained with 2% $AgNO_3$ under UV light for 10 min.

Statistics. Student's T-test was used for comparisons with $p \leq 0.05$ reported as significant.

Results:

The chloride/hydrogen exchanger CLC3 is very strongly expressed in mineralizing osteoblasts, but CLC5 also occurs at significant levels. Following the identification of NHE1 and NHE6 as massively expressed sodium-hydrogen exchangers in the basolateral surface of mineralizing osteoblasts (Liu et al., High capacity Na+/H+ exchange activity in mineralizing osteoblasts. *J Cell Physiol.* 2011 June; 226(6): 1702-12), and reviewing the structure of the osteoblastic surface as an epithelium-like layer expressing the NHEs and NHERF1 specifically at the basolateral surface (Liu et al., Na+/H+ exchanger regulatory factor 1 (NHERF1) directly regulates osteogenesis. *J Biol Chem.* 2012 Dec. 21; 287(52): 43312-21), possible mediators of bone matrix to osteoblast intracellular fluid H+ transport were searched for. Comparing gene screen results for undifferentiated MSC and human osteoblasts in mineral promoting medium showed the striking result that CLC3 went from a median signal in MSC of 29 with p value for expression from 0.12-0.35, to a median signal in osteoblasts of nearly 1,800 with p values uniformly <0.0002. Another CLC, CLC5, was increased in mineralizing osteoblasts, but at lower levels, with p values 0.002 to 0.004 (FIG. 3, A). As expected, the same gene screens showed expected increases in NHE1 and NHE6 to about 1000 and p values of <0.0002 in osteoblasts (not illustrated) (Liu et al., High capacity Na+/H+ exchange activity in mineralizing osteoblasts. *J Cell Physiol.* 2011 June; 226(6): 1702-12, and Liu et al., Na+/H+ exchanger regulatory factor 1 (NHERF1) directly regulates osteogenesis. *J Biol Chem.* 2012 Dec. 21; 287(52):43312-21). Other CLCs were not strongly expressed in osteoblasts (not illustrated). This result was suggestive of a role for Cl−/H+ exchange in osteoblasts. This was then followed up with in situ labeling of mouse bone, without and with CLC3, present (FIG. 3, D). This showed CLC3 labeling consistent with osteoblast membrane expression in surface cells and in the canilicular system. Due to the dominant CLC3 expression, CLC knockout animals were obtained; in CLC3 knockout bone, CLC3 antibody labeling was negative (FIG. 3, D, right panel). This demonstrates that the strong labeling of CLC3, usually present in intracellular vesicles at much lower levels, is not an artifact. However, quantitative PCR (FIG. 3, B) showed, surprisingly, that CLC5 mRNA occurred at about 2/3 of the level relative to β-actin as CLC3.

Since CLC3 was the dominant $Cl^-/H^+$ exchanger, the difference in bone formation was examined between knockout and littermate control mice. The results showed only minor, albeit significant, differences in mice at three months of age (FIG. 3, E-F). Specifically, calcein labels of bone formation were indistinct and dual labels were slightly broad, as examined by blinded observers. In these animals, static histomorphometry showed differences on the order of 5%, with a trend to lower bone volume, trabecular thickness, and increased trabecular spacing in the knockout relative to wild type animals, but none of these reached significance (n=8, not illustrated).

Figure 7:
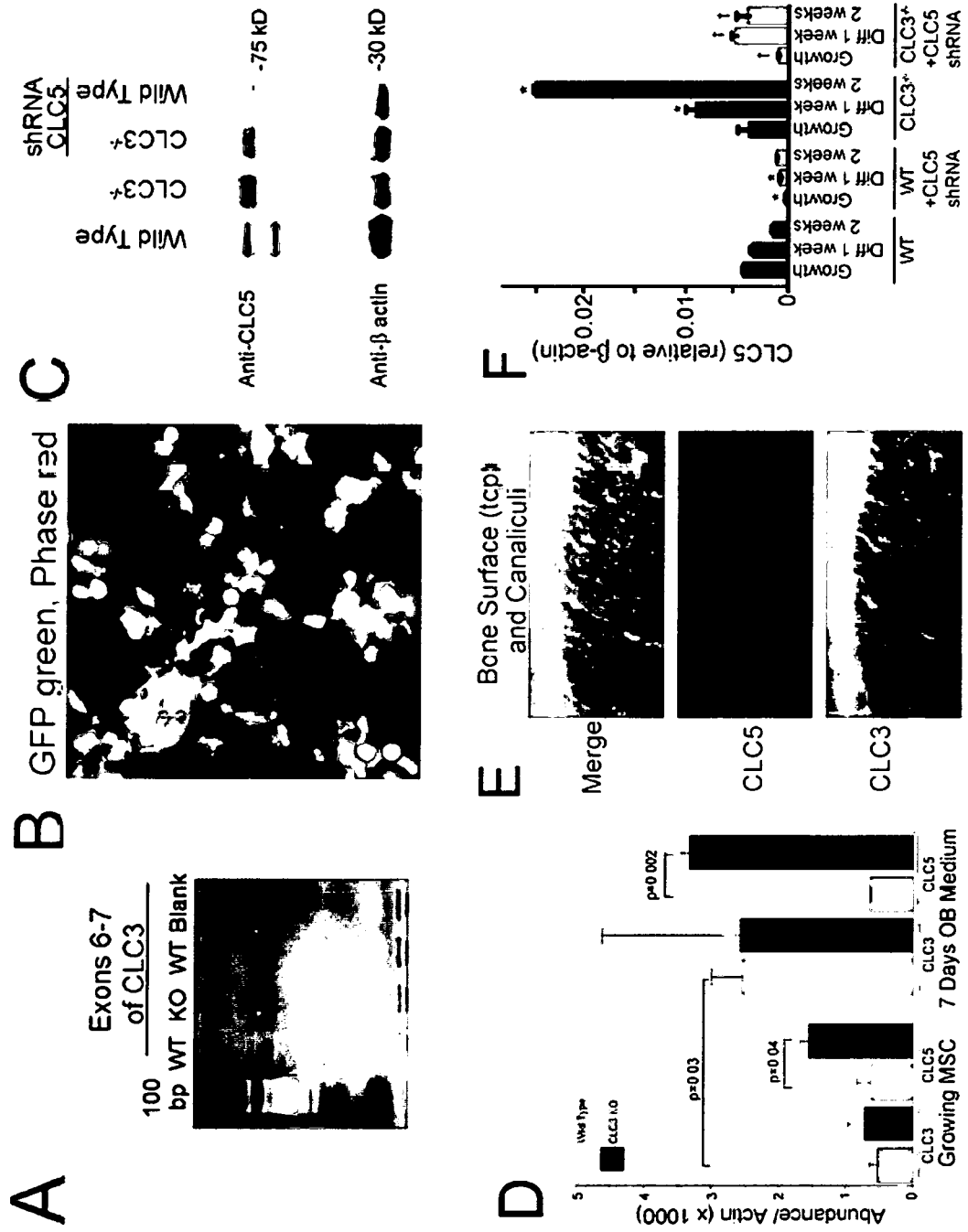
FIG. 7 shows preparation of CLC3 and CLC3/5 null mesenchymal stem cells. A. PCR to probes in exon 6 to 7 showing complete removal in MSC from CLC3 knockout animals. B. Green fluorescent protein to document lentiviral infection of MSC with plasmid carrying both GFP and CLC5 shRNA. Initial infection was ~20% efficient; puromycin selection increased the proportion of knockdown cells 4-5 fold, see PCR data following. C. Western blot of CLC5 in two week osteoblast cultures with and without lentiviral knockdown of CLC5. The increase in CLC5 in the CLC3 null cells is not an artifact, see PCR assays following. With lentiviral shRNA CLC5 protein declined 80-90% relative to matched cultures without shRNA. D. Effect of CLC3 KO on CLC3 and CLC5 expression. The PCR probe for CLC3, to exon 1-2, is unaffected in the knockout, which has a portion of exon 6 and exon 7 deleted. These cells make a nonfunctional CLC3. The probe for CLC5 amplifies a portion of exon 7; primers are listed in FIG. 2. Mean±range for two replicates are shown; one of two experiments with similar results. E. Antibodies demonstrate that CLC3 and CLC5 occur in wild-type murine bone in essentially the same distribution, in the canilicular system and at the basolateral surface of the osteoblasts. High power fields, 400 microns across. Distribution of CLC3 is shown in green, CLC5 in red, and the two merged are shown at the top. F. Effect of lentiviral shRNA on CLC5 in wild type and CLC5 knockout MSC, in growth medium (left of each group) and after one or two weeks in differentiation medium. Differences relative to the wild type control, $p<0.05$, *, differences relative to the CLC3 knockout, $p<0.05$, †. One of two duplicate experiments is shown, each performed in duplicate.

CLC3 knockout osteoblasts have increased CLC5 expression. To confirm the genotype, the KO and wild type (WT) alleles were identified by PCR with genomic DNA using primers specific to the targeted region in exons 6-7 (FIG. 7, A). Western blotting revealed low levels of ClC3 protein in ClCN3−/− mouse; defective protein is present, but nonfunctional (not shown). On the other hand, examination for CLC5 expression showed that, in CLC3 knockout cells, a consistent, dramatic, and significant increase in CLC5 expression by Western blot (FIG. 7, C) or quantitative PCR in osteoblasts cultured for one week in osteoblast differentiation medium (FIG. 7, D). Western blots also demonstrated the practicality of reducing CLC5 expression by lentiviral shRNA in wild type or CLC3−/− cells (FIG. 7, C). If CLC5 may compensate for CLC3, the two should have overlapping occurrence in bone. Dual labeling of wild type bone for CLC3 and CLC5 confirmed this (FIG. 7, D). Additional studies of CLC5 expression in wild type and CLC3−/− cells in growth medium and in differentiation medium, with and without lentiviral CLC5 shRNA confirmed greatly increased CLC5 in CLC3−/− cells, and that the shRNA reduced CLC5 by about 80% in either cell type (FIG. 7, E).

Figure 8:
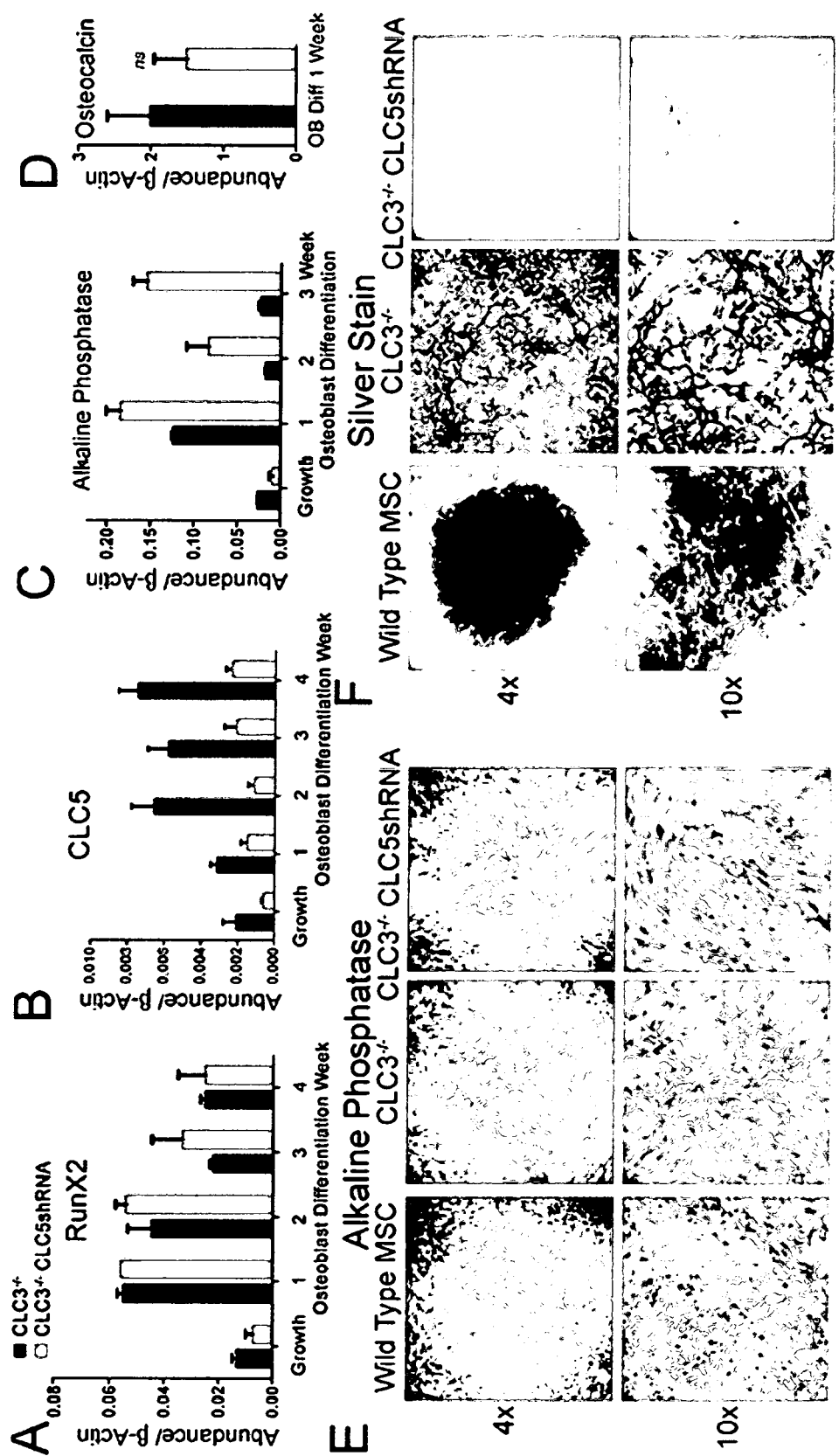
FIG. 8 shows the effect of CLC3 absence, and of CLC5 knockdown in CLC3−/− cells, on bone matrix production and mineralization. Low power photographs 3.5 mm across at 4×, and 1.6 mm at 10×. A. Lentiviral suppression of CLC5 has no effect on mRNA for the master regulator RunX2, during growth or differentiation. B. Suppression of CLC5 in the same cultures. Continuous reduction relative to CLC3 null controls. C. Alkaline phosphatase mRNA was consistently higher in the CLC knockout cells with CLC5 suppressed as well. Expression dropped in week 4 to much lower levels, and is not shown. D. Expression of osteocalcin peaked at week 1 in differentiation medium. It was not significantly affected by suppression of CLC5. Other times had much lower expression and are not shown. E. Alkaline phosphatase activity was similar in wild type cells or CLC3−/− cells with and without CLC5 shRNA. The CLC3−/− cells had remarkable trabecular mineral (see FIG. 8, F) In the CLC3 knockout and control, alkaline phosphatase was strongest adjacent to mineralizing matrix (see FIG. 9). F. Mineral was nodular in the control, trabecular in the CLC3−/−, and absent in the CLC3−/− cells with CLC5 shRNA. The columns of mineral in CLC3−/− cells were bordered by alkaline phosphatase (see FIG. 9). This pattern of bone differentiation was remarkably consistent in different isolates of CLC3−/− cells, and in several replicates of each isolate. Wild type and CLC3−/− mineral included lacunae, or osteocyte-like cells (see FIG. 9).

Effect of eliminating both CLC3 and CLC5 on bone formation in vitro. While selection for CLC5 null cells was imperfect (FIG. 7, B, E), the method tends to make cells that have very low levels of target mRNA while a minority of cells are resistant to puromycin selection; it was hypothesized that the majority of CLC3 negative and CLC5 knockdown cells would determine the phenotype, and studied effects on osteoblast differentiation. In keeping with specificity of CLC3/5 for transport but not differentiation, suppression of CLC5 has no effect on mRNA for the transcription factor RunX2 during growth or differentiation (FIG. 8, A). Suppression of CLC5 in the same samples used for the RunX2 assays was documented (FIG. 8, B). On the other hand, alkaline phosphatase mRNA was consistently higher in the CLC knockout cells with CLC5 also suppressed (FIG. 8, C). The bone-specific matrix protein osteocalcin was greatly elevated at week 1 in differentiation medium relative to growth medium, but osteocalcin was not significantly affected by suppression of CLC5 (FIG. 8, D) Alkaline phosphatase activity, using 37 -naphthol phosphate substrate, was similar at low magnification in wild type cells, or in CLC3−/− cells with and without CLC5 shRNA (FIG. 8, E). On the other hand, alkaline phosphatase occurred in a patchy pattern in the wild type cells, while other cell types had more uniform alkaline phosphatase expressing cells. Similarly, mineral deposition had a nodular pattern in wild type cells.

In CLC3−/− cells, there was a remarkable development, trabecular bone. In bone differentiation in vitro, mineralization always has been in patchy and irregular. The highly branching trabeculae may be a key observation, a practical method of creating trabecular bone in vitro; this occurred in CLC3−/− cells from different MSC isolations and in multiple separate tissue cultures.

Figure 9:
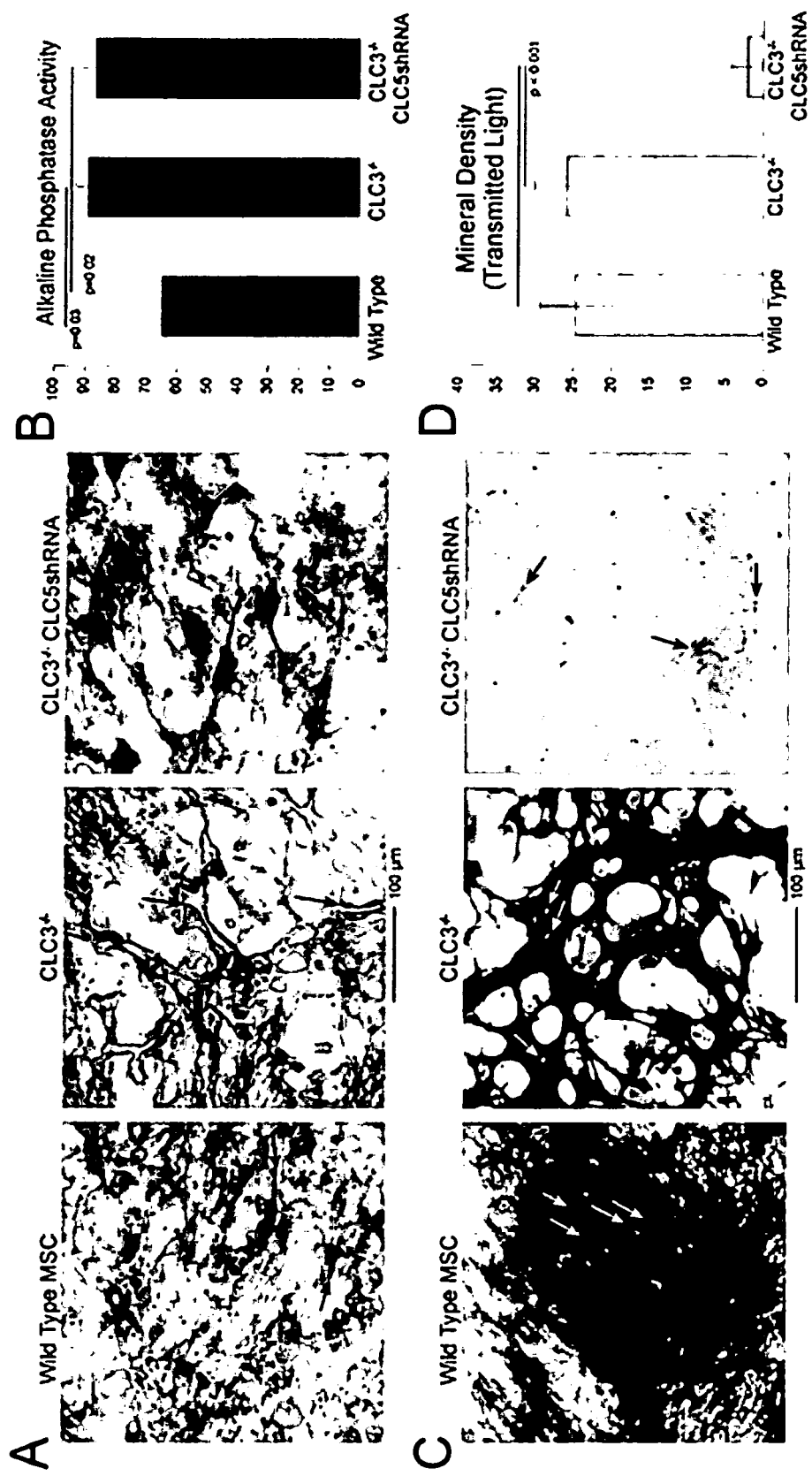
FIG. 9 shows the characteristics of alkaline phosphatase and mineral deposition at high power in wild type, CLC3−/−, and CLC3−/− with CLC5 shRNA cells. A. Alkaline phosphatase. There is focal dense alkaline phosphatase in wild type (left) and in CLC3−/−, CLC5 shRNA cells right, in fine linear areas consistent with cell surface and cell process-associated activity. In the CLC3−/− cells there is also dense alkaline phosphatase adjacent to most of the trabecular bone, which is refractile unstained material here (arrows, center panel). B. Quantitative alkaline phosphatase activity. Activity in wild type cells was strong in nodules, but overall slightly, but significantly, less than the cells with modified CLCs. There was no difference between CLC3 negative and CLC3 negative CLC5 shRNA cells. C. Silver stain for bone mineral. In wild type and in CLC3−/− cells, lacunae indicate that cells incorporated in the matrix. In the CLC3−/−+CLC5 shRNA cells, no significant mineral occurs, although minor amounts of linear labeling are seen in the pattern similar to strong cell surface associated alkaline phosphatase activity (A, right panel, arrows), suggesting non-specific phosphate precipitation at sites of very high alkaline phosphatase (see text). D. Densitometry for mineral, quantified as dark matter in transmitted light, in the three cell types. This avoids variability in silver labeling of mineralized matrix. There is no difference in overall mineral deposition in wild type and CLC3−/− cells, despite the large difference in the pattern of mineralized matrix. The CLC3−/−+CLC5 shRNA cells make no meaningful mineralized matrix.

In keeping with the hypothesis that Cl−/H+ exchange supports mineral deposition, mineral was uniformly absent in CLC3−/− cells with CLC5 shRNA. While some residual CLC5 occurred, clearly this was insufficient to support any significant mineralization. Properties of bone matrix in CLC defective cells at high resolution. In all cell types, alkaline phosphatase occurred in fine linear patterns consistent with cell surface associated activity (FIG. 9, A), in keeping with its cell surface expression as established in other contexts (Magnusson et al., Isoforms of bone alkaline phosphatase: characterization and origin in human trabecular and cortical bone. *J Bone Miner Res*. 1999 November; 14(11):1926-33). In the CLC3−/− cells dense alkaline phosphatase activity occurred adjacent the trabecular bone, in keeping with its distribution at the bone-attached osteoblast surface in vivo (FIG. 9, A, middle). Quantitative alkaline phosphatase activity showed slightly higher activity in the cells with modified CLCs, but no difference between CLC3−/− and CLC3−/−, CLC5 shRNA (FIG. 9, B).

Silver stain for bone mineral was positive in wild type and CLC3−/− cells; at high power, gaps in the matrix were consistent with lacunae reflecting bodies of cells incorporated in the matrix (osteocytes) (FIG. 9, C, left and middle panels). In CLC3−/−, CLC5 shRNA cells, no significant mineral was deposited. There were minor amounts of linear labeling at high power, in the pattern similar to strong cell surface associated alkaline phosphatase activity. This may reflect that, in the presence of the glycerol-2-phosphate substrate at high concentration (10 mM), some calcium-phosphate precipitate is likely to occur outside of cell-bounded matrix production, similar to calcification of hypertrophic cartilage. Mineral was quantified as dark material in transmitted light to avoid differences in silver nitrate staining (FIG. 9, D). Overall mineral deposition in wild type and CLC3−/− cells was the same, notwithstanding the profound difference in the pattern of mineralized matrix. The CLC3−/−, CLC5 shRNA cells made no significant mineral.

While the present invention is described with reference to several distinct embodiments, those skilled in the art may make modifications and alterations without departing from the scope and spirit. Accordingly, the above detailed description is intended to be illustrative rather than restrictive.

We claim:

1. A method of producing trabecular bone material, comprising: culturing CLC3 knockout osteoblasts ex vivo in culture medium for a length of time such that trabecular bone material is produced.

2. The method of claim 1, wherein the CLC3 knockout osteoblasts are obtained by culturing CLC3 knockout mesenchymal stem cells or osteoblast precursor cells in osteoblast differentiation medium.

3. The method of claim 2, wherein the mesenchymal stem cells or osteoblast precursor cells are human or murine.

4. The method of claim 2, wherein the osteoblast differentiation medium comprises ascorbic acid and a phosphate source.

5. The method of claim 4, wherein the osteoblast differentiation medium does not contain a glucocorticoid.

6. The method of claim 4, wherein the phosphate source is glycerol-2-phosphate.

7. The method of claim 1, wherein the osteoblasts are human or murine.

8. The method of claim 1, wherein the CLC3 knockout knockdown osteoblasts are prepared by:
   a. isolating CLC3 knockout mesenchymal stem cells or osteoblast precursor cells from a CLC3 knockout transgenic animal; and
   b. differentiating the CLC3 knockout mesenchymal stem cells or osteoblast precursor cells to an osteoblast phenotype, thereby producing a CLC3 knockout osteoblast capable of producing trabecular bone material.

* * * * *

UNITED STATES PATENT AND TRADEMARK OFFICE
CERTIFICATE OF CORRECTION

PATENT NO. : 11,060,060 B2
APPLICATION NO. : 15/760452
DATED : July 13, 2021
INVENTOR(S) : Harry Colbert Blair et al.

It is certified that error appears in the above-identified patent and that said Letters Patent is hereby corrected as shown below:

On the Title Page

Column 1, Item (71) Applicants, Lines 8-9, delete "Washington University in St. Louis," and insert -- Washington University, --

In the Specification

Column 1, Line 7, delete "pf" and insert -- of --

Column 1, Line 10, delete "62/219,480," and insert -- 62/219,480 --

In the Claims

Column 29, Line 22, Claim 8, before "osteoblasts" delete "knockdown"

Signed and Sealed this
Nineteenth Day of July, 2022

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 2457
<212> TYPE: DNA
<213> ORGANISM: Mus musculus

<400> SEQUENCE: 1
atggagtctg agcagctgtt ccatagaggc tactatagaa acagctacaa cagcataacc      60
agcgcgagta gcgatgagga gctcctagat ggagcaggtg ccattatgga ctttcagact     120
tctgaagatg acaatttgtt agacggggac acagcagctg gaactcatta tacaatgaca     180
aatggaggca gcattaatag ctctacacac ttgctggatc ttttagatga gcctatccca     240
ggtgtcggta cctacgatga tttccatact attgactggg tgcgagagaa gtgtaaggac     300
agagaaaggc acagacggat caacagtaaa aaaaaagaat cagcatggga aatgacaaaa     360
agtctgtatg acgcctggtc aggatggctt gtcgttacac tgacgggact ggcatcaggg     420
gcactagctg gattgataga cattgctgct gactggatga ctgacctgaa ggagggcatc     480
tgcctcagtg cattgtggta caaccatgaa cagtgttgtt ggggctctaa tgagacaacg     540
tttgaagaga gggataaatg tccacagtgg aaaacatggg cagagttaat cattggccaa     600
gcagagggcc ctggatctta tcatgaac tacatcatgt atatctttg ggctttgagt         660 tttgcctttc ttgcagtttc tttggtgaaa gtatttgctc catatgcctg tggctctgga     720
attccagaga ttaaaactat tttgagtgga tttatcatca gaggatactt gggaaaatgg     780
actttaatga ttaaaactat cacgttagtg ctggctgtgg catcaggttt gagtttagga     840
aaagaaggtc ccctggtaca tgttgcctgc tgctgtggaa atatcttttc ctacctcttt     900
ccaaagtata gcaccaatga agctaaaaag agggaggtgc tgtcagccgc ctcagctgct     960
ggggtttctg tggcttttgg tgcaccgatc ggaggagttc ttttttagctt ggaggaggtt    1020 agctattatt ttcctctcaa aactttatgg agatcatttt ttgctgcttt ggtggcagca    1080
```

-continued

```
tttgttttga gatccatcaa tccatttggt aacagccgtc tggtcctctt ttatgtggag    1140
tatcatacac catggtacct ttttgaactg tttccttta ttctcctagg ggtatttgga    1200
gggctttggg gagcttttt tattagggca aatattgcct ggtgtcgtcg acgcaagtcc    1260
accaaatttg gaaagtatcc tgttctcgaa gtcattattg ttgcagccat tactgctgtg    1320
atagccttcc ccaacccata cacaaggctc aacaccagtg aactgattaa agagctgttt    1380
acagattgtg ggccgttgga atcctcctct ctctgtgact acagaaatga catgaatgcc    1440
agtaaaattg ttgacgatat tcctgaccgt ccagcaggcg ttggagtata ttcagctatc    1500
tggcagttgt gcctagcgct catatttaaa ataataatga cagtattcac ttttggtatc    1560
aaggtcccgt caggcttgtt tatccccagc atggccattg agccattgc agggagaatt    1620 gtggggatcg ctgtggagca gcttgcctac tatcaccacg actggtttat cttcaaggag    1680
tggtgtgagg ttgggctga ctgcatcact cccgggctgt atgccatggt tggggctgct    1740
gcgtgcttag gtggtgtgac aagaatgact gtgtctctgg tggttattgt ttttgaactt    1800
actggaggct tggaatatat tgttcctctt atggctgcag taatgaccag taaatgggtt    1860
ggtgatgcct ttggtaggga aggtatttat gaagcacaca tccgactaaa tgggtaccct    1920
ttcttggatg caaagaaga attcactcat acaaccctgg ctgctgatgt tatgagacct    1980
cgaagaagtg accctcccctt agctgttttg acacaggaca atatgacagt agatgacata    2040
gaaaacatga ttaatgaaac cagctataat ggctttcctg ttataatgtc aaaagaatct    2100
cagagattag tgggatttgc cctcagaaga gacctgacta ttgcaataga agtgccaga    2160 aaaaacaag aagggattgt tggcagttct cgggtgtgtt ttgcacagca tactccatct    2220
cttccagcag aaagtccacg gccattaaaa ctgagaagca tccttgacat gagccccttt    2280
acagtgacag accacacccc aatggagatt gtggtagaca tctttcgaaa gcttggtctg    2340
aggcagtgcc ttgtaactca caacggacgc ctccttggca ttataacaaa aaaagatatc    2400
ctccgtcata tggcccagac ggcaaaccaa gaccccgctt caataatgtt caactga      2457
```

<210> SEQ ID NO 2
<211> LENGTH: 58
<212> TYPE: DNA
<213> ORGANISM: Artificial Sequence
<220> FEATURE:
<223> OTHER INFORMATION: DNA sequence for shRNA directed to Clcn5

<400> SEQUENCE: 2

```
ccggcctatg atgatttcaa cacaactcga gttgtgttga aatcatcata ggttttg       58
```

<210> SEQ ID NO 3
<211> LENGTH: 21
<212> TYPE: DNA
<213> ORGANISM: Artificial Sequence
<220> FEATURE:
<223> OTHER INFORMATION: forward primer sequence for Actin

<400> SEQUENCE: 3

```
gatatcgctg cgctggtcgt c                                              21
```

<210> SEQ ID NO 4
<211> LENGTH: 24
<212> TYPE: DNA
<213> ORGANISM: Artificial Sequence
<220> FEATURE:
<223> OTHER INFORMATION: reverse primer sequence for Actin

```
<400> SEQUENCE: 4
acgcagctca ttgtagaagg tgtg                                              24

<210> SEQ ID NO 5
<211> LENGTH: 24
<212> TYPE: DNA
<213> ORGANISM: Artificial Sequence
<220> FEATURE:
<223> OTHER INFORMATION: forward primer sequence for Alp

<400> SEQUENCE: 5
atcggaacaa cctgactgac cctt                                              24

<210> SEQ ID NO 6
<211> LENGTH: 24
<212> TYPE: DNA
<213> ORGANISM: Artificial Sequence
<220> FEATURE:
<223> OTHER INFORMATION: reverse primer sequence for Alp

<400> SEQUENCE: 6
accctcatga tgtccgtggt caat                                              24

<210> SEQ ID NO 7
<211> LENGTH: 20
<212> TYPE: DNA
<213> ORGANISM: Artificial Sequence
<220> FEATURE:
<223> OTHER INFORMATION: forward primer sequence for Clcn3

<400> SEQUENCE: 7
ccaagacccc gcttcaataa                                                   20

<210> SEQ ID NO 8
<211> LENGTH: 20
<212> TYPE: DNA
<213> ORGANISM: Artificial Sequence
<220> FEATURE:
<223> OTHER INFORMATION: reverse primer sequence for Clcn3

<400> SEQUENCE: 8
cgagtcccgc agattaaaga                                                   20

<210> SEQ ID NO 9
<211> LENGTH: 21
<212> TYPE: DNA
<213> ORGANISM: Artificial Sequence
<220> FEATURE:
<223> OTHER INFORMATION: forward primer sequence for Clcn5

<400> SEQUENCE: 9
gaggagccaa tccctggtgt a                                                 21

<210> SEQ ID NO 10
<211> LENGTH: 21
<212> TYPE: DNA
<213> ORGANISM: Artificial Sequence
<220> FEATURE:
<223> OTHER INFORMATION: reverse primer sequence for Clcn5
```

```
<400> SEQUENCE: 10
ttggtaatct ctcggtgcct a                                              21

<210> SEQ ID NO 11
<211> LENGTH: 24
<212> TYPE: DNA
<213> ORGANISM: Artificial Sequence
<220> FEATURE:
<223> OTHER INFORMATION: forward primer sequence for Col1

<400> SEQUENCE: 11
ttctcctggc aaagacggac tcaa                                           24

<210> SEQ ID NO 12
<211> LENGTH: 24
<212> TYPE: DNA
<213> ORGANISM: Artificial Sequence
<220> FEATURE:
<223> OTHER INFORMATION: reverse primer sequence for Col1

<400> SEQUENCE: 12
aggaagctga agtcataacc gcca                                           24

<210> SEQ ID NO 13
<211> LENGTH: 24
<212> TYPE: DNA
<213> ORGANISM: Artificial Sequence
<220> FEATURE:
<223> OTHER INFORMATION: forward primer sequence for Ocn

<400> SEQUENCE: 13
accatctttc tgctcactct gctg                                           24

<210> SEQ ID NO 14
<211> LENGTH: 24
<212> TYPE: DNA
<213> ORGANISM: Artificial Sequence
<220> FEATURE:
<223> OTHER INFORMATION: reverse primer sequence for Ocn

<400> SEQUENCE: 14
tattgccctc ctgcttggac atga                                           24

<210> SEQ ID NO 15
<211> LENGTH: 23
<212> TYPE: DNA
<213> ORGANISM: Artificial Sequence
<220> FEATURE:
<223> OTHER INFORMATION: forward primer sequence for Runx2

<400> SEQUENCE: 15
atgatgacac tgccacctct gac                                            23

<210> SEQ ID NO 16
<211> LENGTH: 22
<212> TYPE: DNA
<213> ORGANISM: Artificial Sequence
<220> FEATURE:
<223> OTHER INFORMATION: reverse primer sequence for Runx2

<400> SEQUENCE: 16
actgcctggg gtctgaaaaa gg                                             22
```